(12) United States Patent
Young et al.

(10) Patent No.: US 12,685,347 B2
(45) Date of Patent: Jul. 21, 2026

---

(54) WEARABLE WITH TEMPERATURE CONTROL

(71) Applicant: Cube Recovery Company, Stamford, CT (US)

(72) Inventors: Aaron Young, Stamford, CT (US); Alex Richardson, Stamford, CT (US)

(73) Assignee: CUBE RECOVERY COMPANY, Los Angeles, CA (US)

( * ) Notice: Subject to any disclaimer, the term of this patent is extended or adjusted under 35 U.S.C. 154(b) by 231 days.

(21) Appl. No.: 18/359,848

(22) Filed: Jul. 26, 2023

(65) Prior Publication Data

US 2024/0057697 A1 Feb. 22, 2024

Related U.S. Application Data

(60) Provisional application No. 63/465,772, filed on May 11, 2023, provisional application No. 63/392,427, filed on Jul. 26, 2022.

(51) Int. Cl.
| | |
|---|---|
| *A41D 13/005* | (2006.01) |
| *A42B 1/008* | (2021.01) |
| *A61F 5/01* | (2006.01) |

(52) U.S. Cl.
CPC .......... *A41D 13/0053* (2013.01); *A42B 1/008* (2013.01); *A61F 5/0106* (2013.01); *A61F 5/0111* (2013.01)

(58) Field of Classification Search
CPC ... A41D 13/0053; A42B 1/008; A61F 5/0106; A61F 5/0111; A61F 2007/0042;
(Continued)

(56) References Cited

U.S. PATENT DOCUMENTS

| | | | |
|---|---|---|---|
| 4,962,761 A | * 10/1990 | Golden ..................... | A61F 7/02 607/104 |
| 6,024,720 A | 2/2000 | Chandler et al. | |

(Continued)

FOREIGN PATENT DOCUMENTS

| | | | | |
|---|---|---|---|---|
| FR | 3134512 A1 | * 10/2023 | ............... | A61F 5/34 |
| KR | 20160001242 A | 1/2016 | | |

(Continued)

OTHER PUBLICATIONS

Kristie L. Ebi et al., Heat and Health 1—Hot weather and heat extremes: health risks, pp. 698-708 (11 pgs), vol. 398 Aug. 21, 2021. www.thelancet.com.

(Continued)

*Primary Examiner* — Beverly M Flanagan
(74) *Attorney, Agent, or Firm* — PILLSBURY WINTHROP SHAW PITTMAN LLP

(57) ABSTRACT

A wearable device having a body-to-liquid heat exchanger, configured to exchange heat between a user's body and a liquid, the body-to-liquid heat exchanger comprising a conformal bladder defining a serpentine portion of a liquid-flow path; a first conduit placing an inlet to the liquid-flow path in fluid communication with an outlet of a liquid-to-ambient-air heat exchanger; a second conduit placing an outlet of the liquid-flow path in fluid communication with an inlet of the liquid-to-ambient-air heat exchanger; and the liquid-to-ambient-air heat exchanger coupled to the first conduit and the second conduit.

27 Claims, 28 Drawing Sheets

(58) Field of Classification Search
 CPC ...... A61F 2007/0044; A61F 2007/0002; A61F
   2007/0054; A61F 2007/0075; A61F
   2007/0233
 USPC .......................................................... 607/104
 See application file for complete search history.

(56) References Cited

U.S. PATENT DOCUMENTS

| | | | | |
|---|---|---|---|---|
| 7,959,657 | B1 * | 6/2011 | Harsy | A61F 7/007 607/104 |
| 10,350,108 | B1 * | 7/2019 | Rittman, III | A61F 7/02 |
| 2009/0069731 | A1 * | 3/2009 | Parish | A61H 1/006 601/150 |
| 2010/0031674 | A1 * | 2/2010 | Aldrich | F25B 21/04 62/3.2 |
| 2011/0277485 | A1 * | 11/2011 | Yang | F28F 1/22 62/3.2 |
| 2012/0227432 | A1 * | 9/2012 | Creech | A41D 13/0053 62/259.3 |
| 2013/0238042 | A1 * | 9/2013 | Gildersleeve | A61N 1/36021 607/104 |
| 2013/0331914 | A1 * | 12/2013 | Lee | A61F 7/007 607/96 |
| 2016/0206018 | A1 * | 7/2016 | Barbret | A41D 13/0053 |
| 2017/0224520 | A1 * | 8/2017 | Karasahin | A61B 5/11 |
| 2019/0296206 | A1 * | 9/2019 | Kemp | H10N 10/17 |
| 2019/0350752 | A1 * | 11/2019 | Aguiar | A61F 7/02 |
| 2020/0289361 | A1 * | 9/2020 | Tian | A61H 9/0092 |
| 2020/0329788 | A1 * | 10/2020 | Su | A41D 13/0053 |
| 2021/0106459 | A1 * | 4/2021 | Caruso | G06F 3/011 |
| 2021/0154403 | A1 | 5/2021 | Schmitz et al. | |
| 2022/0331135 | A1 * | 10/2022 | Gengrinovitch | A61F 7/007 |
| 2022/0331152 | A1 * | 10/2022 | Young | A61F 7/007 |
| 2023/0276869 | A1 * | 9/2023 | O'Day | A41D 13/005 62/259.3 |

FOREIGN PATENT DOCUMENTS

| | | | | |
|---|---|---|---|---|
| KR | 20210010715 | A | 1/2021 | |
| WO | WO-2016198904 | A1 * | 12/2016 | A61F 7/02 |
| WO | WO-2018175506 | A1 * | 9/2018 | A61F 7/007 |
| WO | WO-2021087047 | A1 * | 5/2021 | A41D 20/005 |
| WO | WO-2022160416 | A1 * | 8/2022 | G05D 23/1919 |
| WO | WO-2022204149 | A1 * | 9/2022 | A41D 13/0053 |

OTHER PUBLICATIONS

Chicas et al., HHS Public Access—Cooling intervention studies among outdoor occupational groups: A review of the literature, Author manuscript Am J Ind Med. Nov. 1, 2020.

Bartkowiak et al., ScienceDirect—Applied Ergonomics, Assessment of an active liquid cooling garment intended for use in a hot environment, pp. 182-189, Jul. 2, 2016.

Ciuha et al., Ergonomics—Cooling efficiency of vests with different cooling concepts over 8-hour trials, vol. 64, No. 5, pp. 625-639, Dec. 23, 2020. https://doi.org/10.1080/00140139.2020.1853820.

Chan et al., International Journal of Occupational Safety and Ergonomics—Evaluating the usability of a commercial cooling vest in the Hong Kong industries, ISSN: 1080-3548, Feb. 28, 2017. https://doi.org/10.1080/10803548.2017.1282237.

Tokizawa et al., Effectiveness of a field-type liquid cooling vest for reducing heat strain while wearing protective clothing, Industrial Health 2020, 58, pp. 63-71, Aug. 9, 2019.

Xu et al., Novel Design of a Personal Liquid Cooling Vest for Improving the Thermal Comfort of Pilots Working in Hot Environments, vol. 2023, 13 pages, Feb. 23, 2023. https://doi.org/10.1155/2023/6666182.

Inoue et al., Partial cooling of the upper body with a water-cooled vest in an environment exceeding body temperature, pp. 1-10, Feb. 22, 2023.

Golbabaei et al., International Journal of Occupational Safety and Ergonomics—The effect of cooling vests on physiological and perceptual responses: a systematic review, Jun. 22, 2020. https://doi.org/10.1080/10803548.2020.1741251.

International Search Report for application No. PCT/US2024/028973 dated Sep. 2, 2024, pp. 1-12.

International Preliminary Report of Patentability for Int'l Application No. PCT/US2024/028973 mailed Nov. 20, 2025, pp. 1-8.

\* cited by examiner

CUBE technology implemented
in a law enforcement
tactical vest

Ports for external liquid cooling

550

552

WEARABLE WITH TEMPERATURE CONTROL

CROSS-REFERENCE TO RELATED APPLICATIONS

The present patent-filing claims the benefit of, and is a non-provisional of, U.S. Provisional Patent Application 63/392,427, titled WEARABLE WITH TEMPERATURE CONTROL, filed 26 Jul. 2022; and U.S. Provisional Patent Application 63/465,772, titled WEARABLE, COMPACT, CONFORMAL, BATTERY-POWERED PERSONAL HEATING AND COOLING DEVICE, filed 11 May 2023. The entire content of each afore-mentioned patent filing is hereby incorporated by reference in its entirety.

BACKGROUND

Modulating temperature of parts of the human body can be useful in a variety of contexts, from modulating overall body temperature for comfort or to enhance performance, to modulating temperature of individual limbs, joints, or organs in more targeted approaches for therapeutic use cases, for instance. Such temperature modulation may include the application of heat or the removal of heat.

SUMMARY

Provided is wearable device having a body-to-liquid heat exchanger, configured to exchange heat between a user's body and a liquid, the body-to-liquid heat exchanger comprising a conformal bladder defining a serpentine portion of a liquid-flow path; a first conduit placing an inlet to the liquid-flow path in fluid communication with an outlet of a liquid-to-ambient-air heat exchanger; a second conduit placing an outlet of the liquid-flow path in fluid communication with an inlet of the liquid-to-ambient-air heat exchanger; and the liquid-to-ambient-air heat exchanger coupled to the first conduit and the second conduit.

Some embodiments include an exoskeleton structure comprising a top segment and a bottom segment, the top segment and bottom segment being coupled together at a hinge that permits the top segment and bottom segment to move relative to each other with at least one degree of freedom; an intermediate support sleeve structure encompassing at least a portion of the exoskeleton structure; and a rigid outer shell configured to encompass the intermediate support sleeve and the exoskeleton structure, wherein the rigid outer shell is attached to a winch system.

Some embodiments include a method of making, using, or controlling the above embodiments.

DESCRIPTION OF FIGURES

The above-mentioned aspects and other aspects of the present techniques will be better understood when the present application is read in view of the following figures in which like numbers indicate similar or identical elements.

Figure 1A:
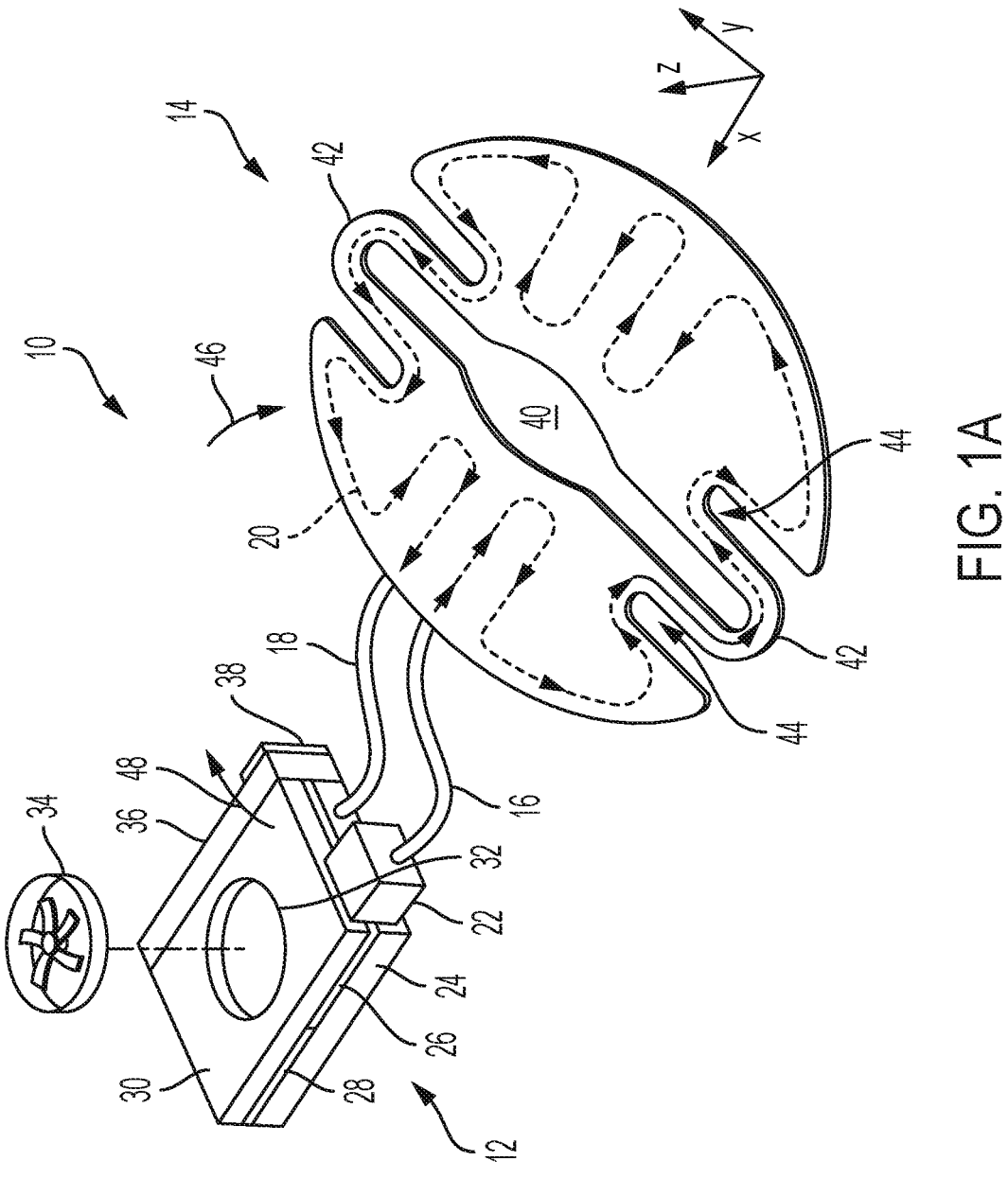
FIG. 1A is a perspective view of a heating and cooling module, in accordance with some embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION

To mitigate the problems described herein, the inventors had to both invent solutions and, in some cases just as importantly, recognize problems overlooked (or not yet foreseen) by others in the field of heat transfer and medical device design. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Many existing wearable heating and cooling devices for the human body have various deficiencies. Some such devices often require the user to freeze an ice pack and are limited in their use once the ice pack has melted. The process of forming the ice and limited duration can be inconvenient in many use cases and make such devices undesirable. Other examples include various types of battery-powered heating or cooling wearable devices. Some such systems often use Peltier chips located at discrete points adjacent to the human body to directly transfer heat from the human body into the Peltier device through contact. Such systems, however, often suffer from limited contact between rigid, relatively-small-in-surface-area Peltier devices and the curved, expansive surface of various portions of the human body. The user often experiences a small number of small, discrete points of conductive cooling or heating on their body. Other examples include systems with forced liquid convection cooling between tubes that heat or cool the human body, adjacent to the tubes, and a fan-cooled heat exchanger with a Peltier device. These systems, however, often suffer from limited heat transfer area from the tubes arrayed on the human body, and such tubes can be expensive and fragile, making such devices unsuitable for scenarios in which the device is subject to heavy usage or extensive movement by the user. It should be emphasized, though, that none of the foregoing issues with such devices constitute disclaimer or disavowal of the discussed techniques, as various embodiments may be used in conjunction with some of those approaches.

Some embodiments mitigate some, and in some cases all, of the above-described issues with an apparatus depicted in FIG. 1A that, in some embodiments, is a dual heat-exchanger (or quad-heat-exchanger), wearable, personal cooling, and heating device 10 with forced convection cooling or heating. In some environments, the device 10 may include an ambient-to-liquid heat exchanger 12, a body-to-liquid heat exchanger 14, a return conduit 16, and outlet conduit 18. These components may circulate a working fluid, like water, through a serpentine path 20 to remove heat from, or add heat to, a portion of a user's body adjacent the heat exchanger 14.

In some embodiments, the heat exchanger 12 may include a pump 22, a working fluid (e.g., liquid) tank 24, Peltier elements 26 and 28, a heat sink 30 with aperture 32, a battery 36, a controller 38, and various sensors that communicate with the controller 38. In some embodiments, the Peltier elements 26 and 28 may be sandwiched between the heat sink 30 and the tank 24 and all three components may be in thermal communication, for example, with thermal paste, like graphene or graphite based thermal paste, disposed between each of the contact surfaces, above and below the Peltier elements (or in some embodiments, the bottom of the Peltier elements may be in contact with the working liquid).

In some embodiments, the dimensions of the heat exchanger 12 may be relatively compact to facilitate movement of a user when wearing the device 10. In some cases, the heat exchanger 12 may be approximately the size of a deck of playing cards. For instance, with a longest dimension in the X direction less than 5 inches, a thickness in the Z dimension less than 1 inch, and a width in the Y direction of less than 4 inches. In some embodiments, the heat exchanger 12 may have a volume of less than 25 cubic inches, like less than 20 cubic inches, less than 10 cubic inches, or less than 5 cubic inches. The heat exchanger 12 may be positioned on a different part of the body from the heat exchanger 14, which is expected to facilitate expanded range of movement in the areas of the body subject to heating or cooling, as the rigid device 12 will not interfere with motion. Further, it may be desirable to reject heat in a different place from where cooling is applied for device efficiency and comfort.

Various techniques may be used to reduce the dimensions of the device 12, including positioning in aperture 32 to receive the fan 34 by which ambient air is forced down and through fins of the heat sink 30 and against a top surface of a portion of the Peltier elements 26 and 28. Or in some embodiments, the direction of airflow may be reversed. Some embodiments may include additional fans 34 or blowers, e.g., one above each Peltier element 26 and 28. In some embodiments, a battery 36 may be positioned adjacent the above-described stack of components, in some embodiments, on either side with multiple batteries. The battery may be, for example, a lithium-ion battery or other suitable power source. In some embodiments, the controller 38 may be integrally positioned in communication with the fan 34 motor, the Peltier elements 26 and 28, a motor of the pump 22, and a temperature sensor, such as one on the tank 24, the heat sink 30, the Peltier elements 26 and 28, or the heat exchanger 14.

In some embodiments, these components of device 10 may define a closed fluid circuit of a working fluid, such as water or water with glycol. In some embodiments, the working fluid may be driven by the pump 22 through a serpentine path inside tank 24, which may be made from a thermally conductive material, such as aluminum, copper, or the like. That serpentine path in tank 24 may result in the working fluid flowing out of the tank 24 into conduit 18 and from conduit 18 into the serpentine path 20 of heat exchanger 14. When flowing through the serpentine path 20, the working fluid may inflate a portion of the heat exchanger 14 to broaden the path and reduce fluid flow resistance. The working fluid may return out of heat exchanger 14 back through tube 16 to the pump 22 to repeat the process. Depending upon the direction of current flow through Peltier elements 26 and 28, the working fluid may be heated relative to the human body in the tank 24 by pulling thermal energy from the environment or cooled relative to the human body in tank 24 by rejecting thermal energy into the environment through the heat sink 30 with the supportive of forced convection from fan 34 on fins of the heat sink 30.

In some embodiments, the fan 34 may be fully recessed or partially recessed into aperture 32 below a top surface of the heat sink 30 to make the heat exchanger 12 more compact. In some embodiments, the pump 22 may have an impeller that is magnetically coupled to an electric motor that is external to the working fluid flow path, such that the working fluid flow path remains fully closed and not pierced by, for an example, an axle between the motor and the impeller. Or, in some embodiments, there may be an axle with seals suitable for preventing the leakage of the working fluid between the motor and the impeller. Or, some embodiments may use other types of pumps, like a peristaltic pump, to circulate the working fluid. Some embodiments may flow approximately a gallon a minute, or less or more, of the working fluid through the fluid circuit.

Some embodiments may include a relatively flexible heat exchanger 14 that is conformal to the human body and can be inflated by the working fluid partially to define the serpentine path 20. In some embodiments, the heat exchanger 14 is referred to as a bladder. Some heat exchangers 14 may be formed by die cutting two sheets of a flexible, waterproof fabric like polypropylene Pax in the shape illustrated in FIG. 1, aligning those two cut pieces, and thermally welding the two cut pieces together (e.g., melting the polypropylene in discrete areas). In some embodiments, the thermal weld may run along serpentine path 20, on either side of serpentine path 20, for example, defining a channel between one and two centimeters wide with welds on either side of serpentine path 20. In some embodiments, the thermal weld may be between one and five millimeters wide, for example, approximately two or three millimeters wide. Some embodiments may further include a thermally reflective layer such as a metallic foil adjacent a side of the heat exchanger 14 away from the human body to reflect heat away and when cooling or reflect heat back towards the human body when heating. Some embodiments may further include a comfort layer adjacent the human body such as a layer of fabric.

In some embodiments, the heat exchanger 14 may include various features to make the heat exchanger 14 even more conformal to various portions of the human body. The illustrated heat exchanger 14 is expected to be particularly suitable for joints like knees elbows and shoulders. In some embodiments, the aperture 40 may be positioned over a central portion of the joint, like a kneecap or elbow and the flexible bends 42 may be positioned on either side such that the axis of rotation of the joint is parallel to the y-axis as illustrated. Stress relief apertures 44 may reduce crimping that could cut off fluid flow through the serpentine path 20 and accommodate a more expansive range of movement of the user while wearing the heat exchanger 14 against their body. Some embodiments may include anti-crimping structures disposed between the sheets of polypropylene (or other material) constituting the heat exchanger 14, like at bends 42, such as flexible tubes inserted therebetween before welding. Similar arrangements may be used for other portions of the human body, like ankles wrists necks chest back hips and the like.

The heat exchanger 14 may be biased against the wearer's body with a variety of different techniques. Examples include hook-and-loop straps or an ace bandage wrapped around the joint with the bandage holding the heat exchanger 14 against the joint or other portion of the human body. Other examples include a pneumatic or fluidic actuator positioned on a side of the heat exchanger 14 away from the human body such that when another pump drives another fluid or otherwise pressurizes the other fluid in the actuator, the heat exchanger 14 is pressed by the actuator against the human body or grips the human body. Examples of such actuators include soft robotics actuators like those described in a paper titled Modeling of Soft Fiber Reinforced Bending Actuators in IEEE Transactions on Robotics, Volume 31, No. 3, June 2015, the contents of which are hereby incorporated by reference. Other examples include inflatable balloons or sleeves, like those used in automatic blood-pressure cuffs. In some embodiments, one or more such actuators may, for example, run in the y-direction and cause the heat exchanger 14 to wrap around a limb of the wearer when inflated, thereby causing relatively extensive and movement-compliant contact between the heat exchanger 14 and the human body. Other examples include the winch described below.

Some embodiments may use a hard mechanical cage or other apparatus like those described below to hold the heat exchanger 14 in the desired position and protect the heat exchanger 14. Some embodiments may include as an interface between such a shell and the heat exchanger 14 a bladder cage like those depicted in figures discussed below that is resilient but less resilient than the heat exchanger 14, to impart some structure that still accommodates movement of the human body.

Tank 24 may be machined from a solid block of metal, like a solid block of aluminum, or in some cases it may be diecast. Some embodiments may include a diecast tank 24 and a diecast heat sink 30, for example, joined with a hinge running in the x-direction with an axis of rotation parallel to the x-direction, which in some cases may be formed in a single shot. The diecast hinged component may have the Peltier elements 28 and 26 (or other thermoelectric devices) positioned adjacent to tank 24, and then the heat sink 30 may be sandwiched on top, by pivoting about the hinge, thereby providing a relatively low-cost method of manufacturing components of the heat exchanger 12.

In some embodiments, the module device 10 may be used in a vest, knee-brace, ankle, brace, head band, arm-band, or other garments like those discussed below. In some embodiments, there may be one or more such modules, like 2, 4, 6, or more. In some embodiments, different regions of the wearer's torso may be cooled by different heat exchangers 14, which in some cases may be chained in a serial working fluid flow path, or may be in parallel, in some cases with different heat exchangers 12 coupled to different ones of the heat exchangers 14 in parallel flow paths that do not communicate with one another through fluid flow of the working fluid.

In some embodiments, the vest or other configurations described here may include a phase change material, like a wax, or a chilled ice pack, or a thermally reactive consumable, such as those based on cellulose, iron, activated carbon, vermiculite, and salt. Some embodiments may include a heating pouch that augments the operation of the device 10 and may be swapped out as consumables when used. Some embodiments may augment the operation of the device 10 with a compressed inert gas cartridge, like a $CO_2$ (carbon dioxide or other examples described below) cartridge that releases into the aperture 32 to impart a boost of additional cooling, for example, in a hot ambient environment, for instance, upon being triggered by the controller 38 responsive to detecting such an environment, to provide a cooling boost in difficult ambient environments. These cartridges may be replaceable and controlled by the controller 32 through an electrically actuated valve that causes them to release into the aperture 32 when a boost of cooling is needed. Some embodiments may recirculate the formerly compressed gas back across the heat exchanger for multiple cycles, as that gas may be cooler than ambient for multiple such cycles. For instance, some embodiments may include a gas-flow channel (like a manifold or duct) that receives warmed exhaust gas from an edge portion of the heat exchanger (or a top-central portion, depending on the direction of fluid flow) after that gas has passed along and through fins of the heat exchanger 30. In some cases, the gas-flow channel may loop back around to a gas-inlet portion (e.g., the central part above fan 34 if exhausted over the edge or vice versa) and direct gas flow back against the heat exchanger 30 for multiple cycles. Some embodiments may include a thermostat-driven baffle (e.g., actuated by a thermocouple or a motor at the direction of controller 38 responsive to temperature sensor readings of gas circulating) that opens the gas-flow loop, causing ambient air to be ingested and then exhausted, e.g., in response to detecting that the formerly pressurized gas has reached ambient temperature or has warmed to some threshold temperature.

In some embodiments, the vest may include a magnetically coupled interface to receive the heat exchanger 12 with the aperture 32 facing outward away from the human body, adjacent to the exterior portion of the vest, so it can be clipped to the body. Some embodiments may further include an exhaust vent positioned to receive air coming off of the heat sink 30 and vent it out of the garment, for example, in use cases in the firefighting industry to vent hot air away from the user's body. Some embodiments may include a torsion hole in the vest, for example, in the middle of the user's back, to prevent or impede wrinkling or crimping when the user moves their body. Additionally, or alternatively, some embodiments may include a photo voltaic panel, such as a flexible panel mounted on the back or front of a vest, to charge the battery.

In some embodiments, the battery 30 may be inductively or magnetically charged to extend the battery life. For example, some embodiments may include an inductive charging receptacle, like a coiled wire coupled to the controller 38 to deliver power to the battery 36. In some embodiments, this inductive charging receptacle may be positioned, for example, on the user's back, such that when they sit in a seat of, for example, a delivery vehicle, the battery is charged through a complimentary inductive charging pad with another coil positioned on the driver's seat of the vehicle. In this manner, it is expected that such a user may have their battery charged when driving between houses or between tasks, and then draw upon the battery to maintain their comfort when they leave the vehicle, allowing a battery of modest size to last all day through repeated charging between stops. In some vest use cases, embodiments, such as those designed for farmers or others working outdoors, may include panels for photovoltaic charging. Some embodiments may integrate the modules into industrial equipment and clothing such as welding gear, hazmat suits etc.

In some embodiments, the controller 38 may control the Peltier elements 26 and 28 independently to improve their efficiency. In some embodiments, when Peltier elements are run at maximum capacity, they may operate in a less efficient regime. Some embodiments may cycle between activating Peltier elements 26 and 28 with less than 100% duty cycle on each (e.g., each being between 20 and 80% of the time when cooling or heating), and each being out of phase with the other, such that one of the Peltier elements 26 or 28 is recovering closer to ambient temperature, while the other is driving heating or cooling, and vice versa. Some embodiments may include an array of more than 2, like 4, 6, 8, or more Peltier elements positioned adjacent different portions of the working-fluid flow channel in device 12, and some embodiments may selectively engage different subsets of these Peltier elements (e.g., with less than 100% duty cycles and out of phase in a periodic pattern). In some cases, by the duty cycle and driving voltage or current may be modulated by controller 38 to increase cooling or heating applied.

In some embodiments, the control algorithm may produce outputs that control the fan motor 34, the motor of the pump 22, each of the Peltier elements 26 and 28, and a user interface, like on a smartphone or a wearable computing device like a watch. In some embodiments, the controller 38 may receive inputs from an ambient temperature sensor, wearable computing devices (like a watch with a pulse sensor, a gate sensor, a temperature sensor, a blood glucose sensor, a blood oxygen level sensor, a sleep sensor, or the like), a liquid temperature sensor coupled to the tank 24 or immersed in the working liquid, and the like. In some embodiments, control of the various motors may be implemented with pulse width modulation.

Some embodiments may execute a control algorithm that targets a perceived temperature of the user, which may be different for different people in different environments. Some embodiments may actively learn to control the above-described outputs to maintain a perceived temperature that the user desires. Some embodiments may train a machine learning model executed by the controller based upon biometrics sensed, for example, by a smartwatch or other biometric sensors, and adjustments by a given user. For example, some embodiments may learn to minimize the amount of active user adjustment to target a comfortable perceived temperature of the user.

As noted, the module device 10 may have a variety of use cases, including applying heating or cooling to a knee, a wrist, an ankle, a torso, a neck, a quadricep, a hamstring, a calf, foot, a hand, ears, head, or the like. In some embodiments, the device 10 may be suitable for use when the user is ambulatory and engaging in their work. Various verticals are expected to find the above-described device as useful, including in industrial applications, like those servicing airline equipment on a tarmac, those engaged in delivery in hot or cold climates of packages, tactical use cases in which cooling is applied or heating is applied under a ballistic vest, medical use cases in which therapeutic heating and cooling is applied, and virtual reality use cases in which heating or cooling is applied responsive to gameplay, for example, heating or cooling the user when their character moves into a hot or cold environment, respectively, to increase immersiveness of the game. Some embodiments may use the device 10 in motorcycle, construction, military, or bike helmets to cool or heat the user's head. Some embodiments may enhance workouts by cooling the user's hands, e.g., through a mitt or glove, or by having heat exchanger 14 wrapped around a handle on a treadmill or other exercise equipment. Other use cases may involve cooling or heating things other than the human body, like heating or cooling a food or beverage product, a pharmaceutical, or a biological substance (like blood samples). Contemplated use cases further include cooling electronic devices, like laptop computers, thermal camera sensors, and the like.

Millions of Americans suffer from chronic injuries every year that may benefit from therapeutic icing. A cryo-pod, an ice bath, and an ice bag may be used to recover from a chronic injury. Some methods of recovering from a chronic injury may include non-portability of a cryo-pod, waste of water in an ice bath, single usage of an ice bag, toxic chemicals in an ice bag, and assistance that may be required with an ice bag. Thus, there is a need for a wearable therapeutic device that is portable, does not waste water, does not use toxic chemicals, is reusable, and does not require an assistant to be physically present. Some embodiments mitigate or fully address all of these issues, while others mitigate a subset or other issues. Some embodiments include a device and a method that provide temperature-controlled therapy. Some embodiments include a device and a method that provide therapeutic recovery programs implemented by temperature control.

Wearable devices may be used in various scenarios ranging from athletic recovery to emergency treatment. Such wearable devices may be shaped and constructed differently to serve the athletic community versus the medical community, though a wearable device that is capable of use in multiple situations while being portable and durable is useful as well.

In some embodiments, a wearable therapeutic device includes an exoskeleton structure in which the above module 10 is disposed, the structure comprising a top segment and a bottom segment, the top segment and bottom segment being coupled together at a hinge to move the top segment and bottom segment relative to each other. The wearable therapeutic device may also include an intermediate support sleeve structure encompassing at least a portion of the exoskeleton structure and a rigid outer shell configured to encompass the intermediate support sleeve and the exoskeleton structure, wherein the rigid outer shell includes a winch system.

An exoskeleton composition may be made of a lightweight metal (like an aluminum alloy, titanium alloy, magnesium alloy, etc.), composite materials (like graphene composites, carbon nanotube composites, carbon fiber composites, Kevlar™ composites, fiberglass composites, etc.), or plastic (e.g., ABS, Nylon, PET, PEEK, etc.) to provide a structural support for the wearable device to provide various therapies. The material used may have a specific strength of between 100 kN m/kg and 63,000 kN m/kg, like between 100 kN m/kg and 2500 100 kN m/kg. In some embodiments, the exoskeleton is composed of a durable material capable of withstanding force allowing a user of the wearable to maintain a desired orientation. For example, the exoskeleton structure may provide enough structural support for a wearer to bear his or her entire body weight on the structure.

The exoskeleton structure may be coupled to an intermediate support sleeve structure to provide a layer between the exoskeleton structure and an outer shell. In some embodiments, the intermediate support sleeve is made of a textile material.

In some embodiments, the rigid (e.g., using a material having a Young's modulus of 1 GPa or greater) outer shell structure is made of a plastic material (e.g., acrylonitrile butadiene styrene (ABS), high impact polystyrene (HIPS), expanded polystyrene (EPS)) and other suitable casing materials for providing support and protection for the wearer and the components within the wearable device.

In some embodiments, the wearable device includes a one or more winch systems for providing an adjustable fit of the wearable device to the body part of the wearer. The winch system may include a cable, a drum, a spindle, and a gear configured to adjust the tightness of the wearable device to be worn around the body part of the wearer by pulling and winding up or down a cable or other tether coupled to another part of the device that moves relative to the winch system as the winch system is tightened or loosened. In some embodiments, the winch system of the wearable therapeutic device is a manual winch, an electrical winch, a mechanical drum winch, an air winch, or any other suitable pulley system.

In some embodiments, Peltier thermoelectric heat pumps (referred to as "Peltier devices" or "Peltier modules" interchangeably) may be used for cooling body parts of the user. The Peltier device may transport heat using energy provided by electrical current flow. The efficiency of Peltier cooling may depend on the temperature difference across the module. When a large temperature difference is built up across the module, the temperature gradient drives heat flux in the reverse direction as the direction that the heat is intended to be transported, and the coefficient of performance may be decreased. These cases are problematic in some use cases due to the unfavorable scaling relation regarding the resistive heating of the Peltier module itself combined with increased heat backflow as compared to the heat transported per unit current, especially since larger current leads to increased resistive heating of the module itself, which in turn, requires more heat in total to be dissipated. Therefore, it is beneficial in some cases to remove heat from the Peltier module (e.g., from a hot side of the module) to keep the temperature of the thermal transport energy destination low, which is not to suggest that all embodiments must do this or that any other description is limiting. In some embodiments, the wearable device cools the module solely with air cooling by ambient, untreated air. However, due to the low thermal conductivity and volumetric heat capacity of air, the cooling provided tends to be insufficient for transporting large quantities of heat at a high rate in some use cases (which is not to suggest that this approach or any other is disclaimed). Some embodiments enhance transfer of thermal energy away from the side of the Peltier module (e.g., expel thermal energy) where heat is being deposited through dissipating thermal energy to the surrounding environment.

Icing may be used as a therapy for reducing inflammation and pain during exercise. Since the human body is mostly water, cooling is energetically expensive given that water has a high heat capacity. Ice packs depend on the enthalpy of fusion of ice to absorb the thermal energy. For wearable electronic devices to provide similar or equivalent cooling as compared to a passive system like an ice pack, a comparable amount of energy that is absorbed by the enthalpy of fusion of ice may be transported away from the body (in some cases, during a comparable amount of time). During an icing session, around ~0.300 grams of ice may melt over a time period of less than one hour (like less than 30 minutes), leading to the removal of ~$1\times10^5$ J of energy from the body within 600-1200 seconds. Assuming a reasonable coefficient of performance of 1 for the heat pump (like a Peltier thermoelectric heat pump), ~$2\times10^5$ J may be ejected into the environment to provide a comparable amount of cooling as an ice pack, given that the heat dissipated may include the energy used by the heat pump to transport thermal energy away from the body. The amount of heat to be removed from the system is, in some cases, equivalent to the amount of energy required to vaporize on the order of 100 grams of liquid water, which has a latent heat of vaporization nearly an order of magnitude larger than its latent heat of fusion.

Some embodiments offset the large quantity of energy to be dissipated through the use of vaporization of a substance (which may be carried away from the heat pump by advection or through evaporation at the site of the heat pump or heat sink thermally coupled thereto), which may include any or a combination of the following compounds or mixtures: water, alcohol, propylene glycol, glycerin, or any other harmless substance that has a latent heat of vaporization greater than 15000 J/mol or 300 J/g, such as water, with a latent heat of vaporization of 2257 J/g at ambient pressure at sea level. Some embodiments may perform the vaporization within cooling gas applied to the heat sink 30 above. The aforementioned vaporization process leverages the latent heat of vaporization of the substance and can remove more heat per mass and volume than some other approaches, such as those relying on latent heat of fusion (which is not to suggest that such approaches are disclaimed, as both approaches could be combined in some embodiments). Additionally, air may be transported through the device for the purpose of carrying the vapor from vaporization of the working fluid by the device to the surrounding environment, wherein thermal energy is removed through a combination of (advection driven) convective cooling and evaporative cooling. The advection may be provided by a fan, blower, pump, motor, compressor, or any other system that facilitates bulk transport of gas, air, and/or other fluid, for the purpose of removing the vapor and carrier gas (like ambient air) that has absorbed heat from the device. The energy balance is expected to lead to a greater capability to cool given the limited quantity of energy that is available to power wearable devices, especially due to the lack of need to recondense the harmless substance that is being vaporized and ejected into the surrounding environment external to the thermodynamic system of interest.

In some embodiments, the wearable device includes a heat dissipation system that uses both an advective flux coupled to heat transfer and a phase transition to carry thermal energy away from the heat sink. In some cases, this system may be integrated into the wearable devices described in the documents incorporated by reference. The system may use the vaporization of a harmless substance (like water) to absorb heat at the sites where thermal energy from the body and/or from resistive heating of electronic components are transported to, and uses advection to carry the vaporized substance away.

Some embodiments function with a variety of control systems (examples of which are described in the documents incorporated by reference and elsewhere herein), such as intermittent or alternating power of vapor according to time intervals or measurement of temperature, that is vapor controlled by a thermo-sensor activated or deactivated at specified temperatures; including vapor control of system, such as deactivating the device power when vapor level is empty, and/or generating a display message to "fill or refill" vapor source, for example. Some embodiments may operate at less than 24 volts, for example less than or equal to 12 volts, to mitigate weight, noise, and thermal load from higher-voltage components.

In some cases, the present techniques may be integrated with the devices and processes described in U.S. patent application Ser. Nos. 17/520,479; 17/725,229; 63/244,073; and 63/310,046, the contents of which are hereby incorporated by reference.

In some embodiments, a wearable device for providing therapeutic recovery can be coupled with a profile that is set by a person (e.g., a user/wearer of an embodiment, a trainer of the user, etc.) with a recovery program for a user (e.g., an athlete), where the athlete inputs progress (e.g., temperature, time, diet, sleep, stress level, etc.). For example, an athlete has a knee injury, and his trainer wants him to adhere to a recovery program that includes repeated icing and heating of the knee. The athlete may some embodiments that include an integrated communication device that allows the trainer to control/modify/oversee the recovery of the athlete's knee. In use, the athlete may apply the wearable device to his knee and turn the wearable device on. The trainer may then remotely configure a 20-minute recovery program that includes the wearable device applying heat for 5 minutes, cooling for 5 minutes, and so on until the 20 minutes is up. Alternatively, the athlete may utilize an onboard display to manually configure the wearable device, for example, if the wearable device is too hot or cold for his or her comfort.

In some embodiments, a wearable device for providing therapeutic recovery is wearable on one or more portions of a wearer's body and provides icing or heating in intervals. For example, a user may program an embodiment to provide heat and/or cold (e.g., icing) in user-definable time intervals (e.g., 15 minutes, 20 minutes). Some embodiments may also be operated manually through a device interface or an application or app (e.g., an application configured to communicate via a Bluetooth™ (or other forms of communication) of a mobile computing device upon which the application runs with a similar interface on the wearable device).

In some embodiments, the wearable device (or server or mobile computing device with which is communicates) securely transmits a message to another person (e.g., a doctor, a physical therapist, a trainer) and securely receives messages from the same. The message may concern an instruction from the other person to the user of some embodiments, progress of the user, and another type of communication between the other person and the user.

In some embodiments, a wearable device for providing therapeutic recovery may be used on various body parts (e.g., ankle, knee, back, wrist, hip, shoulder, chest, hand, foot, head, abdomen, etc.). Some embodiments may be in the form of a vest. Additionally, the wearable device may be configured for use on multiple body parts (e.g., both a wrist and an ankle), in some cases, both left and right sides or just one.

In some embodiments, a wearable device for providing therapeutic recovery may be used by various people (e.g., a high school athlete, a college athlete, a professional athlete, a person recovering from surgery, a laborer). In some embodiments, a wearable device for providing therapeutic recovery may also be used by a person (e.g., a first responder) on another person (e.g., an injured person). The wearable device may be used for medical purposes (e.g., medical icing) and for enhancing athletic performance (e.g., performance cooling). Medical purposes include providing icing or heating concerning hip replacement surgery, knee replacement surgery, anterior cruciate ligament (ACL) surgery, medial collateral ligament (MCL) surgery, rotator cup surgery, herniated disc surgery, back pain, wrist pain, hand pain, ankle injury, etc.

In some embodiments, the wearable device for providing therapeutic recovery is portable, powered by a rechargeable battery, provides cold therapy, is wearable, provides heating and/or cooling in user-definable intervals, and is operable via a native application executing on a user's mobile computing device, like a cell phone.

Expected advantages of some embodiments described herein include the various forms of improvement to thermal efficiency described, temperature control (e.g., adjustability), time control (e.g., adjustability), communication capability (e.g., data updates for efficient assessment), wearability (e.g., long lasting durable mobility), sustainability (e.g., eliminates single-use and reduces water waste), and operability via an application (e.g., allows access via a mobile device). But embodiments are not limited to systems affording these advantages, as various approaches are described that can be used independent and some address other problems, which is not to suggest that any other description is limiting. It is understood that the terms "hotter" and "cooler" refer to temperatures higher and/or lower than a current temperature of the discussed object.

Some embodiments may include a profile in memory that is set by a person (e.g., a user of the invention, a trainer of the user, etc.) with a recovery program for a user of the invention (e.g., an athlete), where the athlete inputs progress (e.g., temperature, time, diet, sleep, stress level, etc.).

Some embodiments may include a wearable that provides icing or heating in intervals. For example, a user of the present invention may program the present invention to provide heat and/or cold (e.g., icing) in user-definable time intervals (e.g., 15 minutes, 20 minutes, etc.). Some embodiments may also be operated manually through a device interface (like buttons or a touchscreen on the wearable device) or an application executing on a client device.

Some embodiments may securely transmit a message to another person (e.g., a doctor, a physical therapist, a trainer, etc.) and securely receives messages from the same. The message may concern an instruction from the other person to the user of the present invention, progress of the user, and another type of communication between the other person and the user.

Figure 1B:
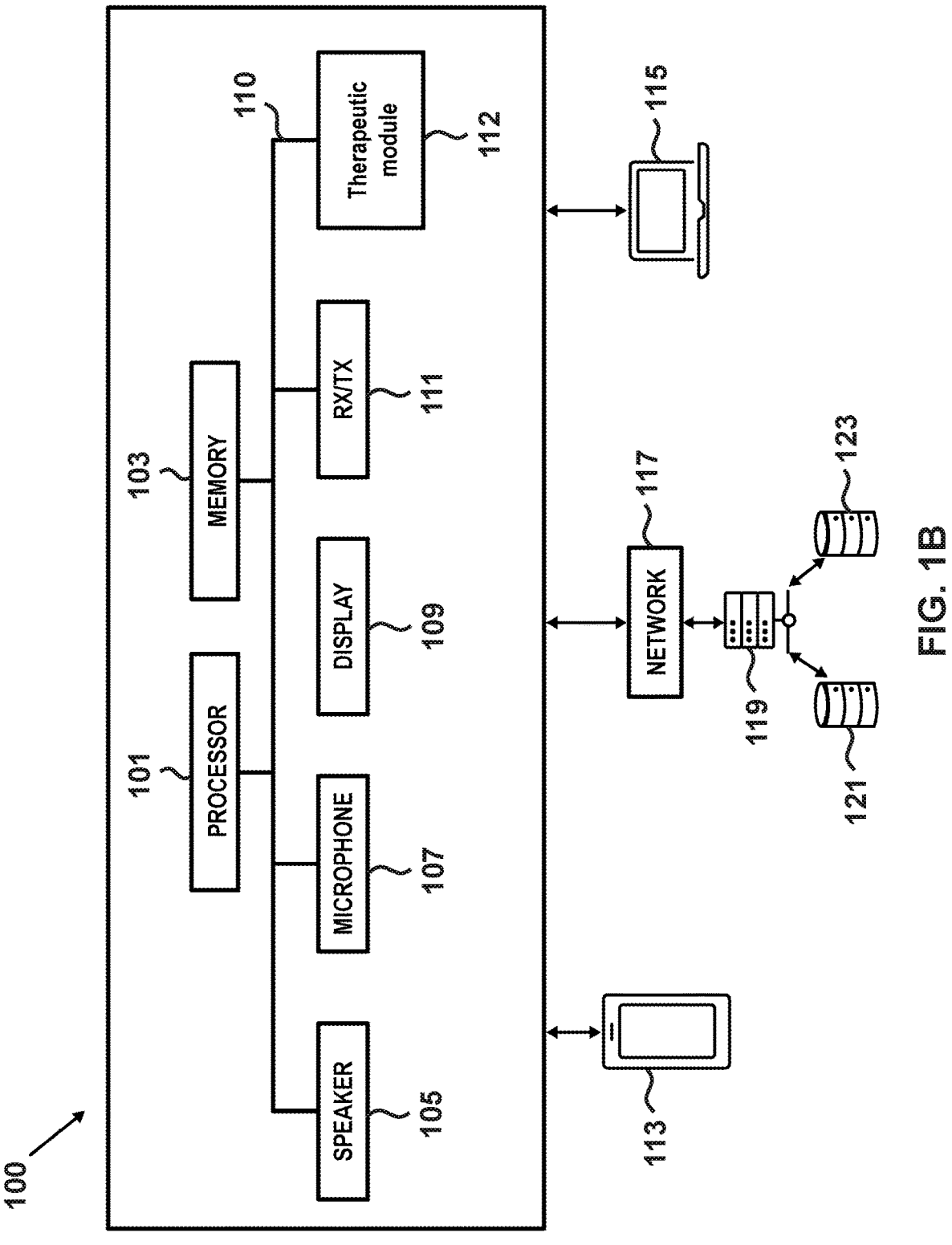
FIG. 1B is a schematic of a wearable therapeutic device and communication devices that may control the device of FIG. 1A, in accordance with some embodiments.

FIG. 1B is a schematic of a wearable device 100 and communication devices in accordance with some embodiments. The device 100 may include and control the operation of the module 10 described above in some embodiments.

As shown in FIG. 1B, the wearable device 100 may include a processor 101 (which may implement controller 38), a memory 103, a speaker 105, a microphone 107, a display 109, a transceiver (RX/TX) 111, and a therapeutic module 112.

The processor 101, the memory 103, the speaker 105, the microphone 107, the display 109, the RX/TX 111, and the therapeutic module 112 may be connected to each other via a bidirectional bus 110.

The processor 101 may control the icing/heating elements, the memory 103, the speaker 105, the microphone 107, the display 109, the RX/TX 111, and the therapeutic module 112 via the bidirectional bus 110.

The memory 103 may store instructions and a user's icing/heating profile, which instruct the processor 101 on how to control the speaker 105, the microphone 107, the display 109, the RX/TX 111, and the therapeutic module 112. The processor 101 may also store in the memory 103 results of operating the therapeutic module 112, instructions input manually by the user via the display 109, and instructions received via the RX/TX 111.

The speaker 105 may output audio from the processor 101 concerning operation of the wearable device 100 and messages received via the RX/TX 111.

The microphone 107 may input audio from the user when the user communicates with another party via the RX/TX 111 or when the user provides audio input to the wearable device 100.

The display 109 may be a touch screen with provides visual output to the user on all aspects of the operation of the wearable device, results of the operation of the wearable device 100, and an input capability to allow the user to manually input instructions and messages into the wearable device 100.

The RX/TX 111 may send and receive messages between the user of the wearable device and another person or device (e.g., a doctor, a trainer, a communication device of the user, a communication device of another party, etc.). The communication devices of the user and another party may include a mobile telephone 113, a laptop computer 115, a server 119, and computers 121 and 123 may be connected to the server 119. Messages to and from the RX/TX 111 may go directly to the communication device (e.g., via Bluetooth™ communication or other forms of communication) or via a network 117 (e.g., the Internet).

The therapeutic module 112 includes icing (e.g., cooling, which does not require reaching freezing temperatures) elements and heating elements that provide icing and heating, respectively, in accordance with the instructions and user profile stored in the memory 103. Additionally, therapeutic module 112 may provide bioelectric stimulation (BES) via transdermal patches, electrodes, micro-needles, hydrogels, exosomes, or other suitable mechanisms. In some embodiments, the therapeutic module 112 includes an ultraviolet light (UV) source for providing antimicrobial and disinfection therapy treatments, e.g., with UV light-emitting diodes being arrayed within the wearable device, for instance around the perimeter of component 46 above.

FIGS. 2A-2M illustrate various view and embodiments of a wearable therapeutic device 200 for a knee or an elbow. In an alternate embodiment, the wearable therapeutic device 200 may communicate with any other communication device (e.g., the laptop computer 115, the server 119, and the computers 121 and 123 directly or via the network 117). The wearable therapeutic device 200 includes all of the components of the wearable device 100 of FIG. 1 but in a wearable form suitable for either a knee or an elbow. The size of the wearable therapeutic device 200 is different for wearing on a knee and wearing on an elbow due to the differences in size of a knee and an elbow.

Figure 2A:
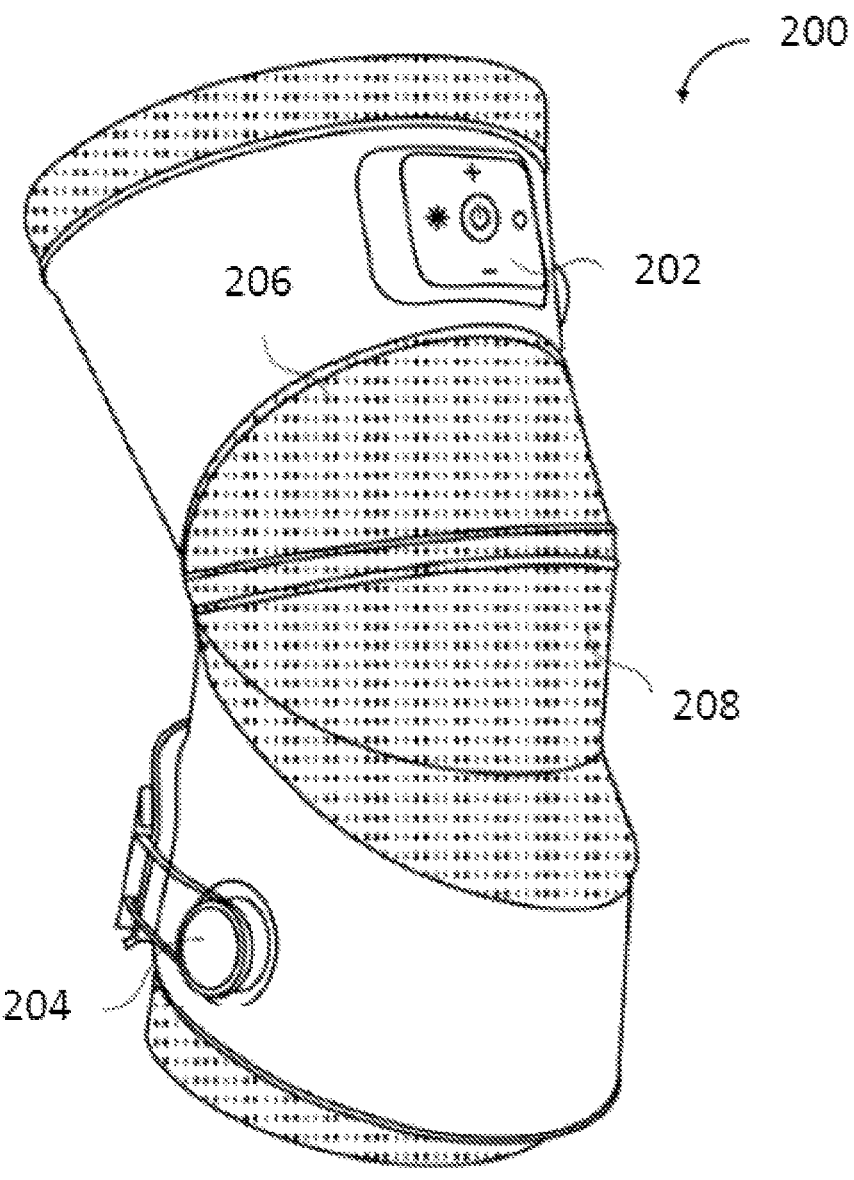
FIGS. 2A-2K illustrate multiple views of embodiments of a wearable therapeutic device for a knee or an elbow and a mobile device of FIG. 1B.

As shown in FIG. 2A, the wearable therapeutic device 200 is illustrated in a first view and includes a display 202, which is an example of the display 109 illustrated in FIG. 1B. Display 202 may be utilized as a control panel to control therapy delivery by the wearable device, communicate with external electronic devices, and select various settings and therapies to be provided. The wearable therapeutic device 200 may operate identically to the wearable device 100 described above. The wearable therapeutic device 200 may further include an adjustment controller 204, a flexible region 206, and a flexible region 208, which may bias component 46 against a user's knee. Each of the flexible regions 206 and 208 may include or be made of textile material that provides a range of motion for the wearable therapeutic device 200. In some embodiments, the flexible regions 206 and 208 are made of an inelastic material (e.g., plastic) to provide stability and protection.

Figure 2B:
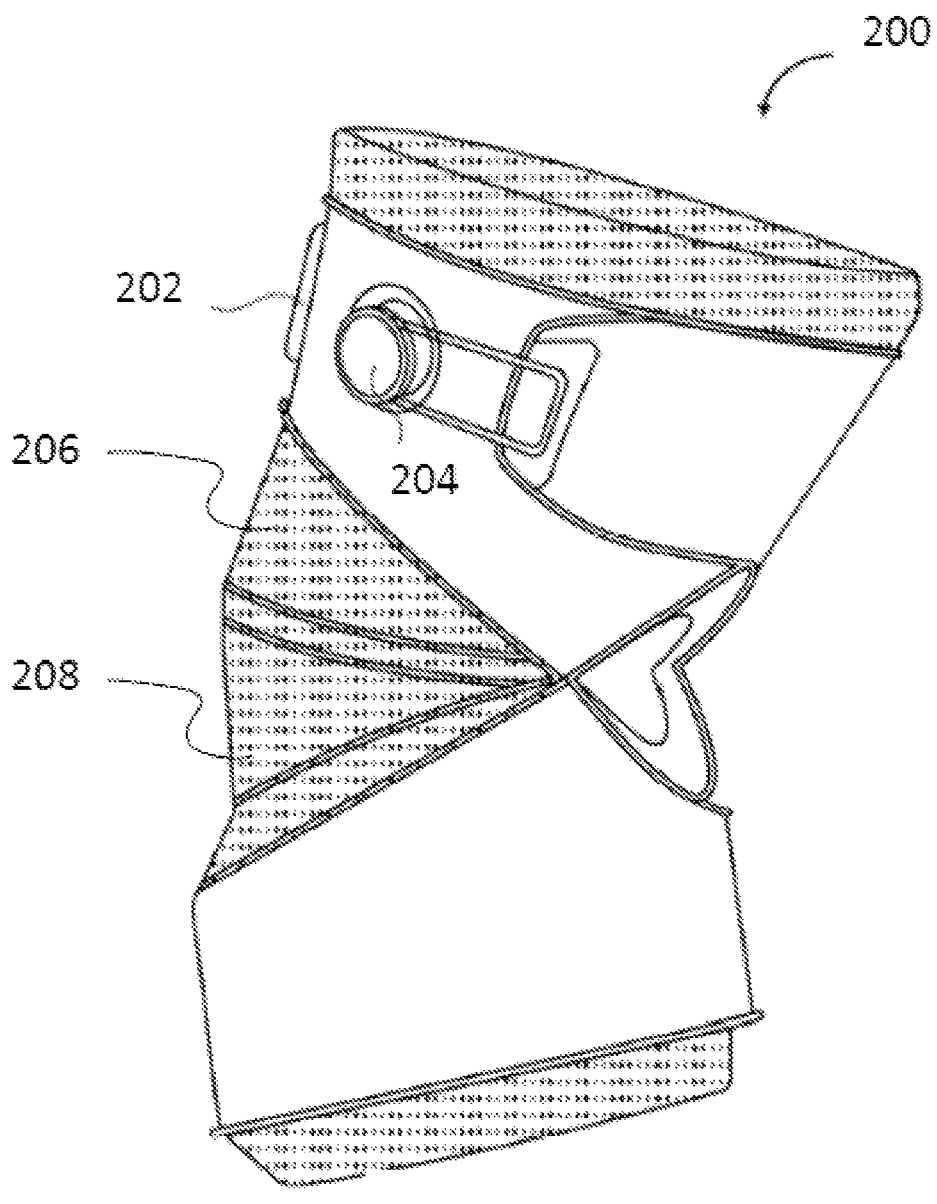

FIG. 2B is a second perspective view of a wearable therapeutic device 200 for a knee of a wearer shown in accordance with some embodiments. FIG. 2B shows a rear-perspective view of wearable therapeutic device 200 that includes a display 202 behind which component 12 may be disposed, adjustment control 204, and flexible regions 206 and 208.

Figure 2C:
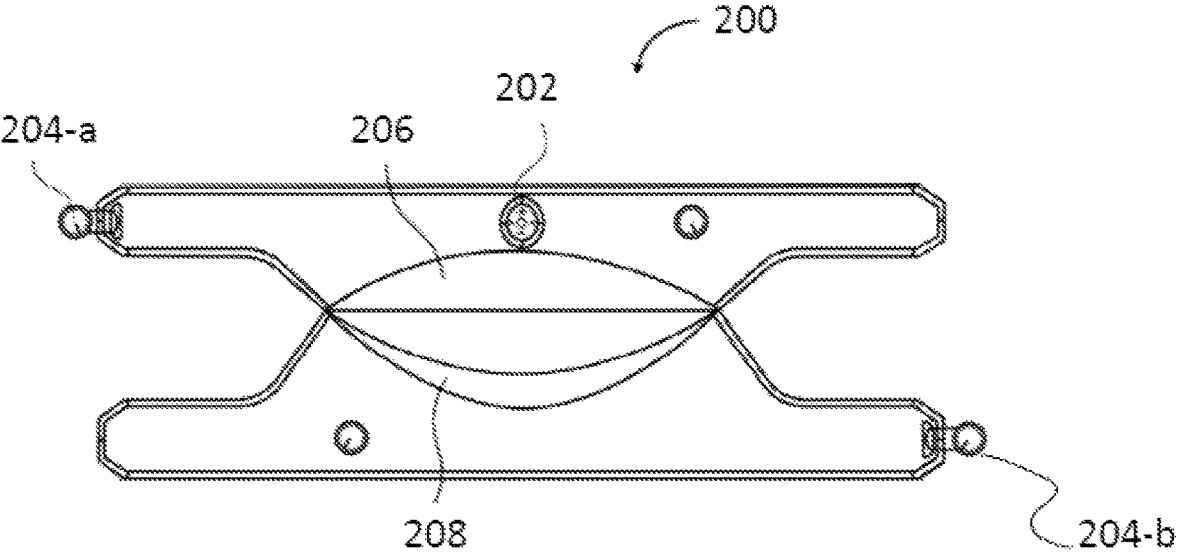

FIG. 2C is a plan view of an un-rolled wearable device (like that of FIGS. 2A-B) for a knee of a wearer shown in accordance with some embodiments. FIG. 2C shows a top plan view of the wearable device including display 202, adjustment controller 204-a and 204-b, and flexible regions 206 and 208. It is understood that various other adjustment controls, flexible regions, and features described herein may not be shown or labeled in FIGS. 2A-2M but may be included. In some embodiments, the features described with reference to subsequent figures are present in the design of FIGS. 2A-M, as is the case with the other examples of depicted wearable devices.

Figure 2D:
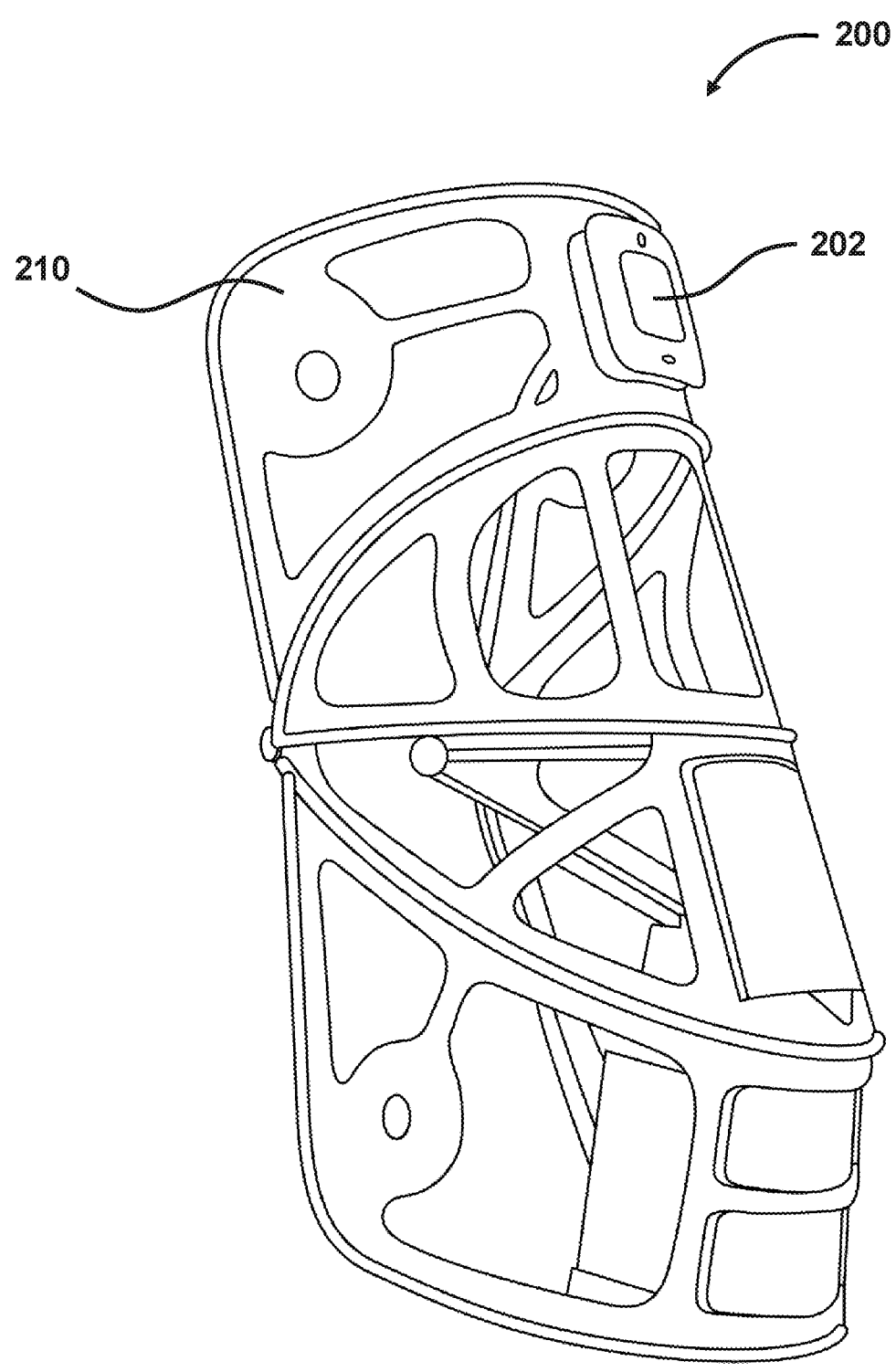

As shown in FIG. 2D, the wearable therapeutic device may include an exoskeleton structure 210 that serves as a base support structure for the wearable therapeutic device 200. In some embodiments, the exoskeleton structure 210 is made of a metallic substance, metal alloy, aluminum composite, plastic, or other suitable material.

Figure 2E:
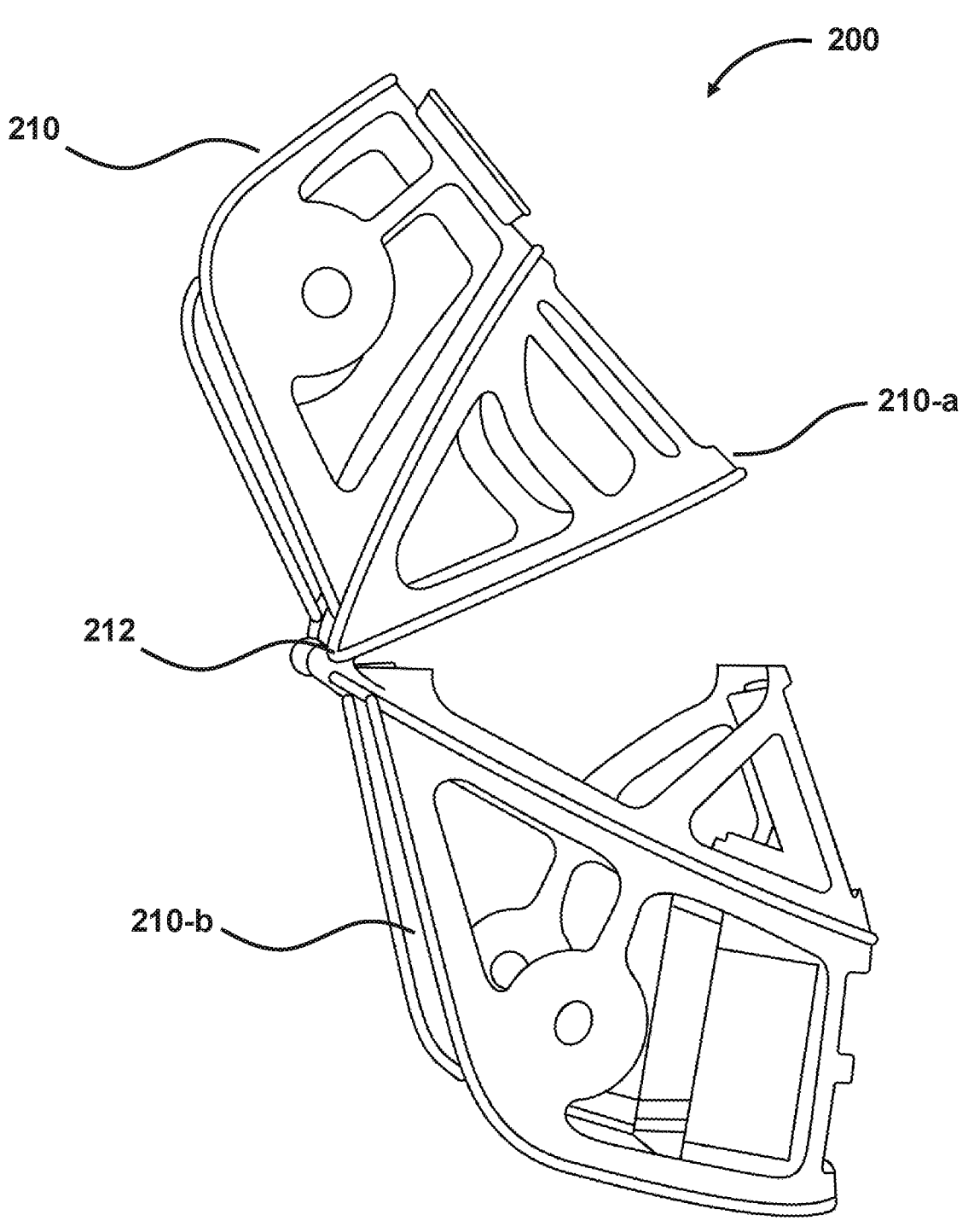

FIG. 2E illustrates the exoskeleton structure 210 of wearable therapeutic device 200 in accordance with some embodiments. The exoskeleton structure 210 in some embodiments includes a top portion 210-a and a bottom portion 210-b. The top portion 210-a and the bottom portion 210-b may be coupled at a hinge joint 212, which may provide a single degree of freedom of relative movement (e.g., rotation about an axis that the device 200 may be positioned to align with a similar axis of rotation of the knee joint). Some embodiments may have a joint with multiple degrees of freedom, e.g., a pivot that is permitted to translate along a channel over less than 2-4 centimeters. The top portion 210-a and bottom portion 210-b are illustrated to show the range of motion capable by affixation by the hinge joint 212. In some embodiments, the top portion 210-a and bottom portion 210-b are adjacent (as illustrated in FIG. 2D). In some embodiments, the top portion 210-a and bottom portion 210-b are configured to separate up to a specified angle (e.g., 300 degrees). The top portion 210-a and bottom portion 210-b are configured to mimic the range of motion of a joint to provide an adjustable fit at a wearer's body part (e.g., knee joint). In some embodiments, the exoskeleton structure includes various patterns, shapes, and negative space that provides visual interest as well as structural support to the wearable therapeutic device.

Figure 2F:
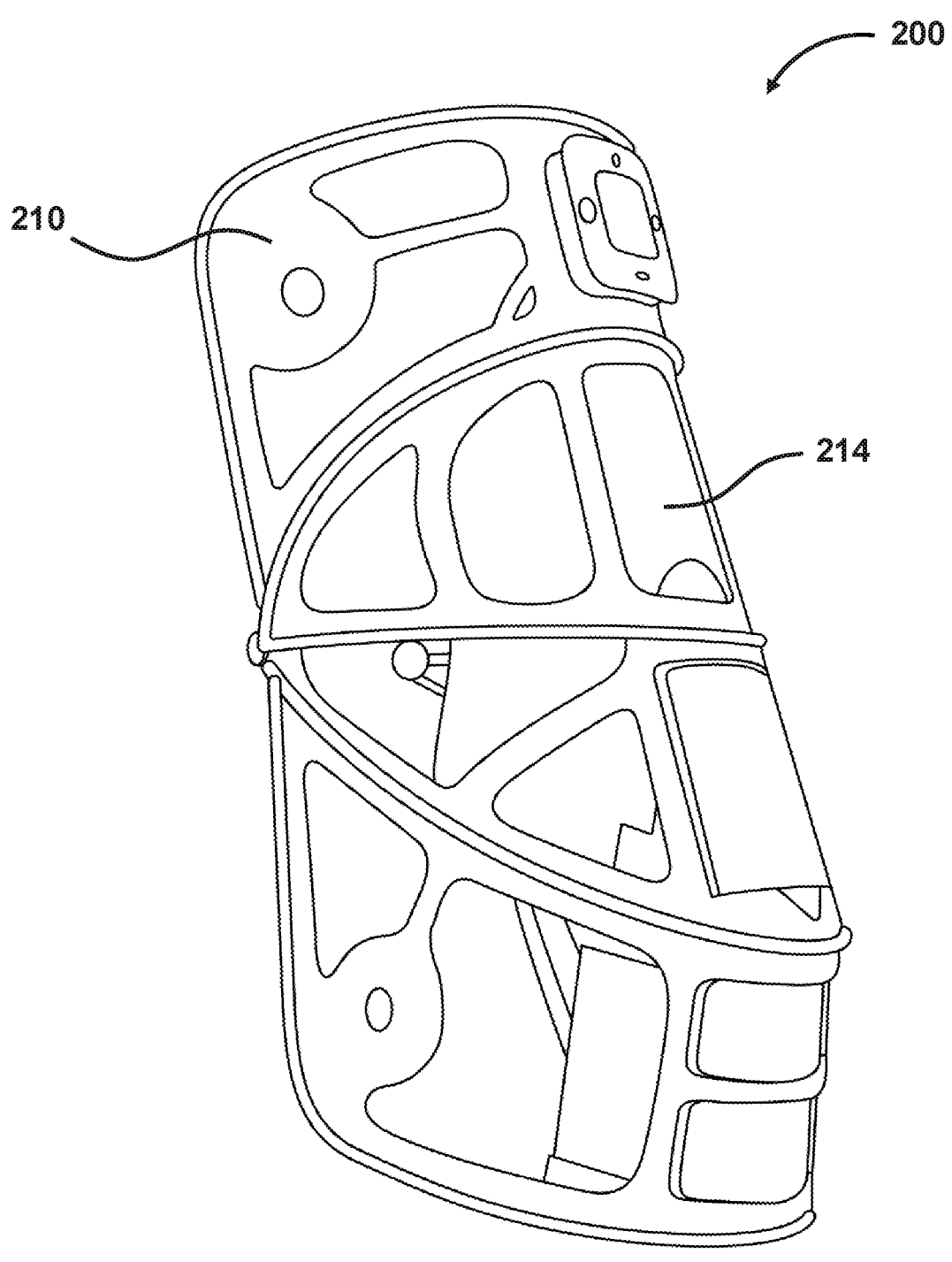

FIG. 2F illustrates the exoskeleton structure 210 of wearable therapeutic device 200 in accordance with some embodiments. The exoskeleton structure 210 may include a pad structure 214 to provide a layer of cushioning and insulation for the wearable therapeutic device 200. In some embodiments, pad structure 214 is configured adjacent to both the top portion 210-a and bottom portion 210-b of the exoskeleton structure. In some embodiments, the pad structure 214 is a foam or silicone-based material to provide insulation and resistant to microbial growth.

Figure 2G:
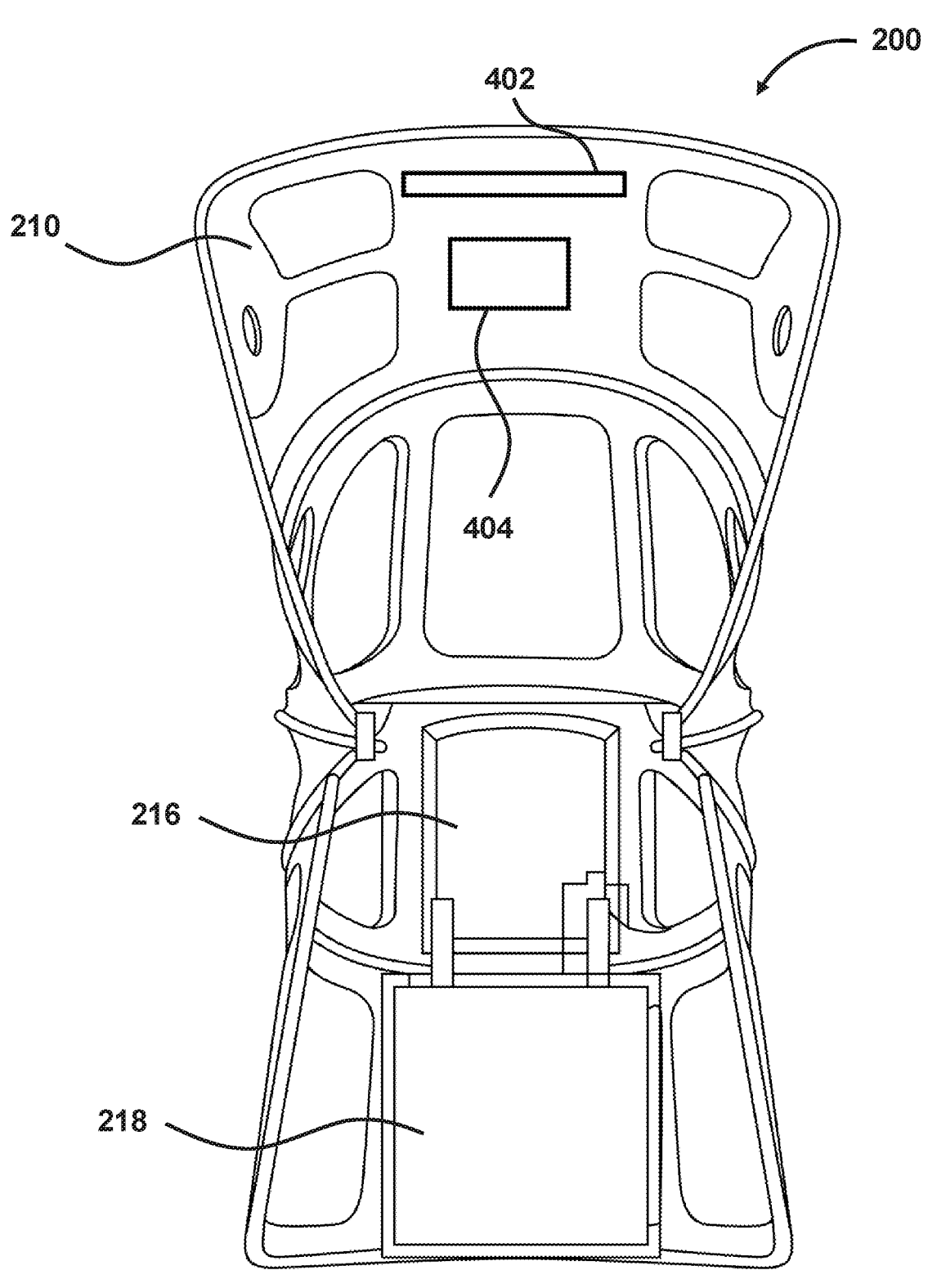

FIG. 2G illustrates the exoskeleton structure 210 of wearable therapeutic device 200 from a rear perspective view in accordance with some embodiments. The exoskeleton structure 210 may provide a housing structure for therapeutic component 216 and therapeutic component 218. In some embodiments, therapeutic component 216 and 218 include a microcontroller, a rechargeable battery, a gas chamber, one or more Peltier devices, one or more ports, electrodes, UV light, microneedles, hydrogens, and exosomes. In some cases, the structure 210 may include an array of UV light-emitting diodes 402 positioned to illuminate an interior of the structure 200 and a patch 404 with an array of microneedles and electrical contacts by which the microneedles are activated by the controller. In some embodiments, a low-impedance sensor (e.g., with an array of electrical contacts or conductive microneedles, like in component 404) to perform impedance-mapping from the localized region of tissue may be included. Some embodiments may use impedance mapping to measure bioelectric physiological changes e.g., inflammation. In some embodiments, the micro-needle may use a topical reagent substance to measure anti-inflammatory protein substrates.

Figure 2H:
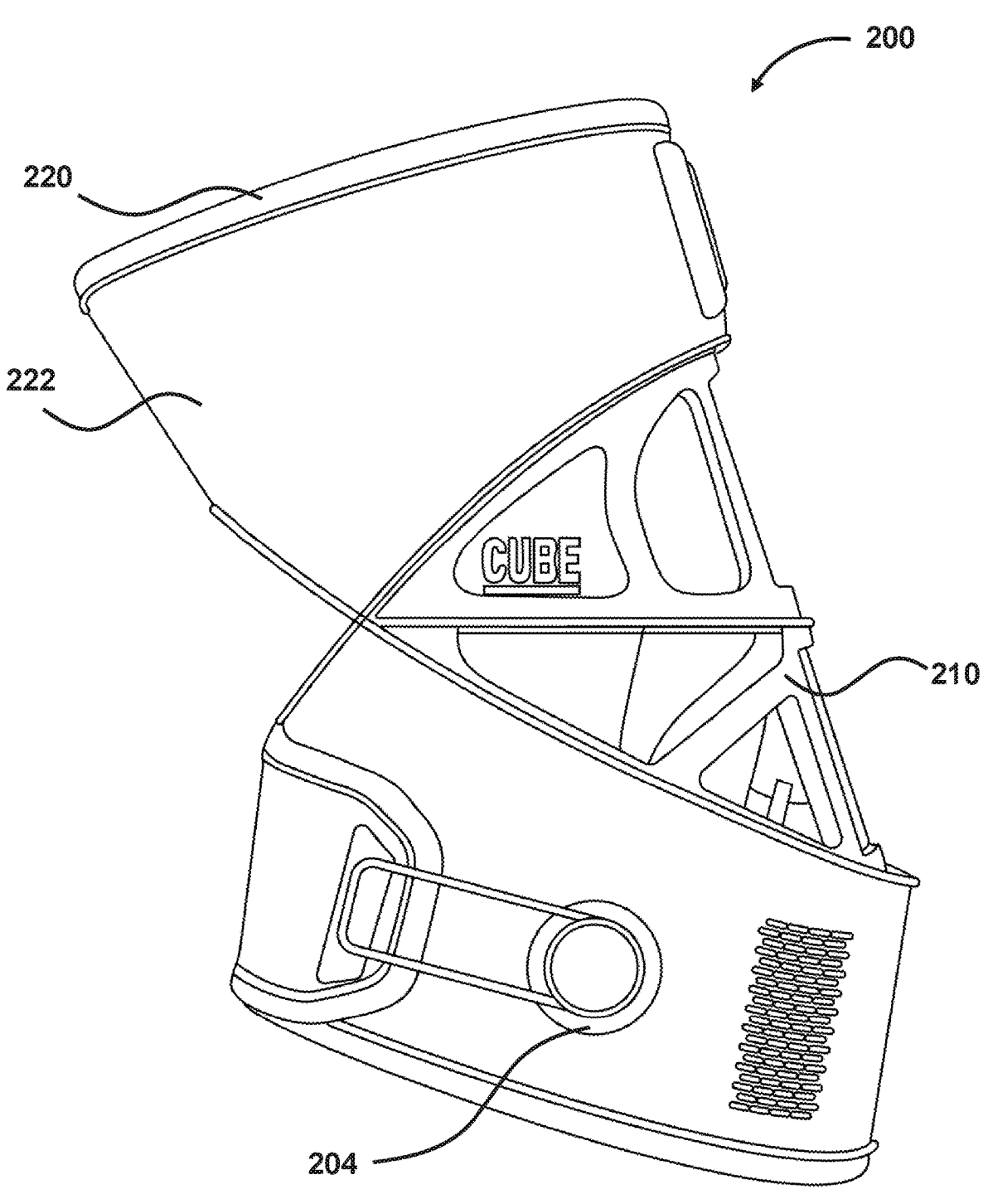

FIG. 2H illustrates the wearable therapeutic device 200 in accordance with some embodiments. The wearable therapeutic device 200 may include exoskeleton 210, textile layer 220, outer shell 222, and adjustment controller 204. Textile layer 220 of the wearable device is provided on a first side of the exoskeleton 210 where a user's limb would contact the wearable device. In some embodiments, textile layer 220 is made of a sweat-wicking, anti-microbial, flexible textile material (e.g., neoprene, polyester, spandex, rayon). Adjustment controller 204 includes a mechanism to configurably tighten and loosen a fit of the wearable therapeutic device 200. In some embodiments, adjustment controller 204 is a winch system. Outer shell 222 may be made of a hard yet flexible material to provide protection to the wearer and contain the components of the wearable device within. Additionally, outer shell 222 may be capable of flexing to allow the wearer to couple and decouple the wearable device from the user's body. Outer shell 222 may include openings for ports for external coupling, ventilation holes, branding, and a strap system coupled with the adjustment controller 204. In some embodiments, outer shell 222 may include discrete sections (e.g., an outer shell top portion to match the shape of top portion of exoskeleton 210-*a* and an outer shell bottom portion to match bottom portion of exoskeleton 210-*b*).

Figure 2I:
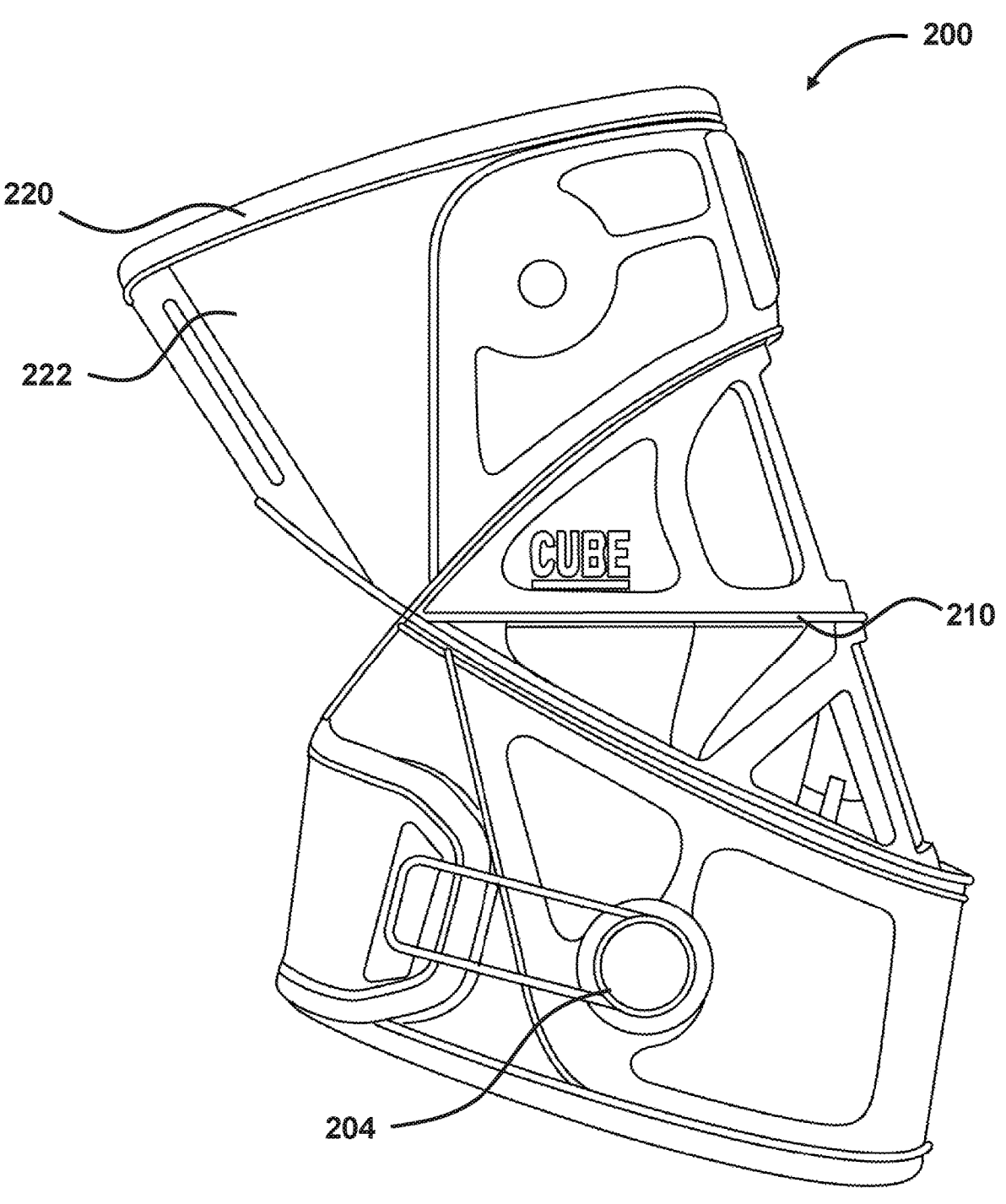
Figure 2J:
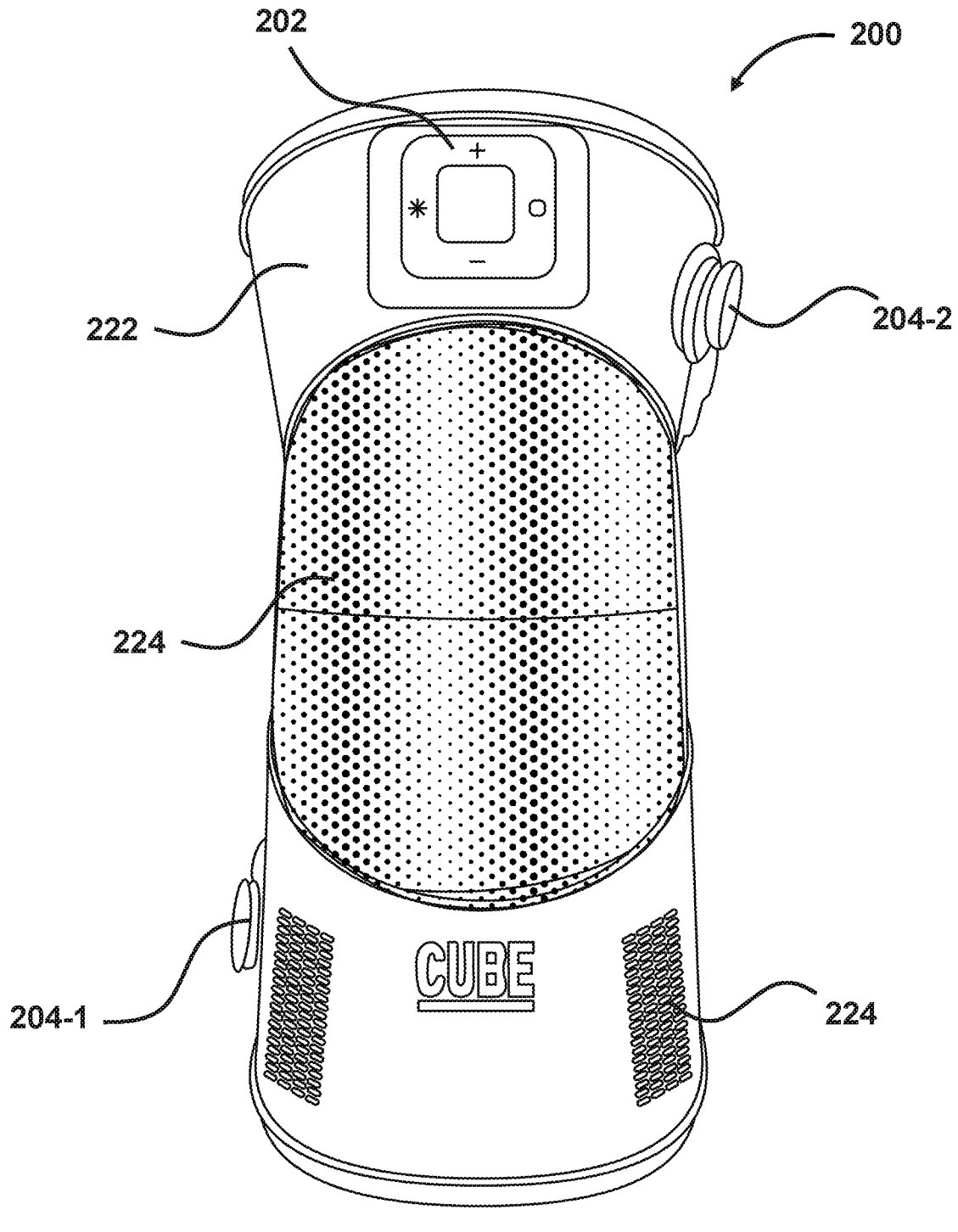

FIG. 2I illustrates the wearable therapeutic device 200 as show in FIG. 2H in accordance with some embodiments. The wearable therapeutic device 200 may include outer shell 222 that is opaque or semi-opaque to allow the structure of the exoskeleton 210 to be seen underneath.

Figure 2K:
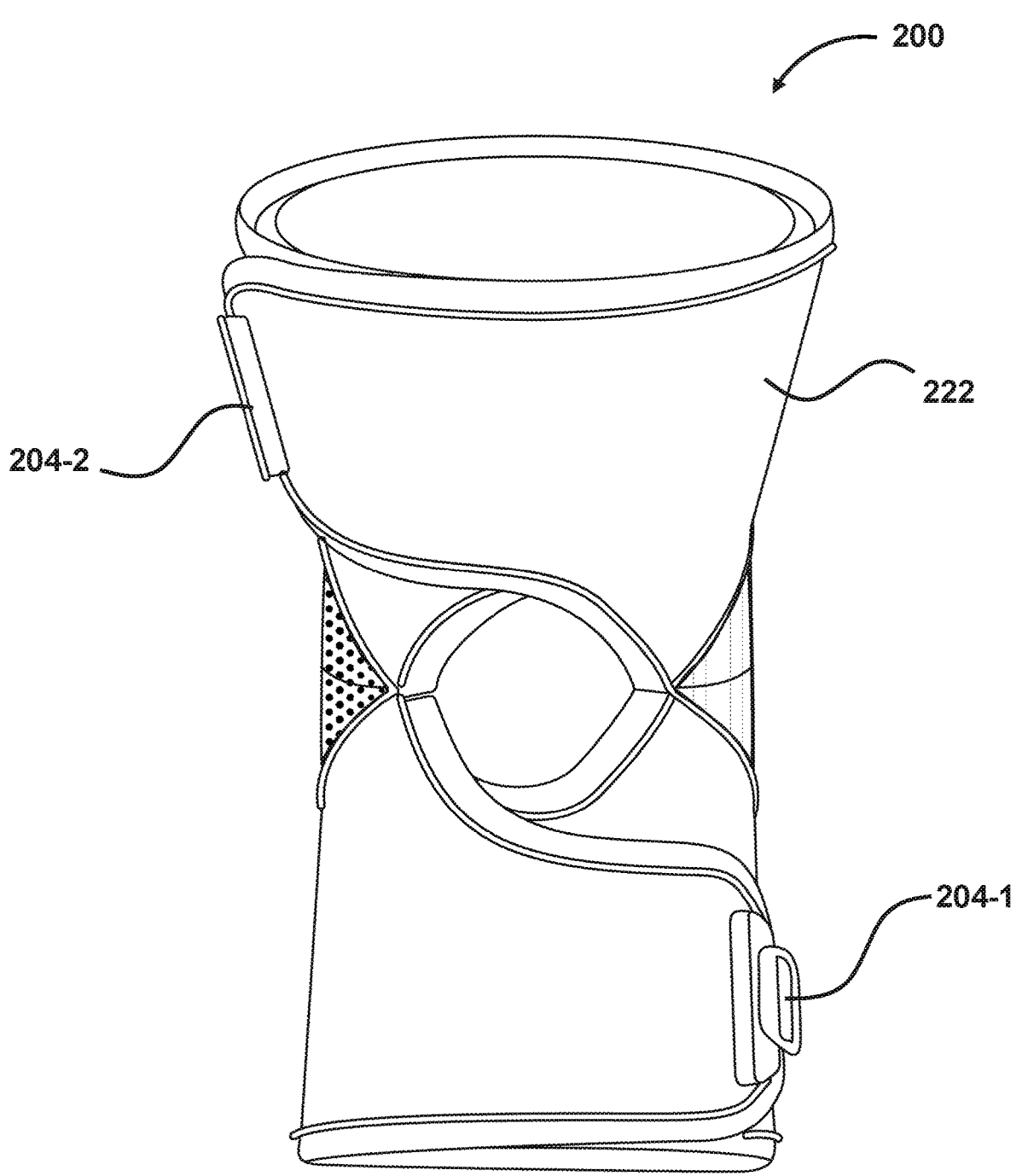

FIG. 2K illustrates a front view of the wearable therapeutic device 200 in accordance with some embodiments. Wearable therapeutic device 200 includes display 202, outer shell 222, adjustment controller 204-1 and 204-2, mesh textile fitting 224 to cover flexible regions 206 and 208, and ventilation structures 226. In some embodiments, the wearable therapeutic device 200 includes multiple adjustment controllers. In some embodiments, the adjustment controllers are a latch system, a hook and loop fastener, snaps, a ratchet system, a magnetic closure, an electromagnetic closure, a mechanical winch system, a pulley system, or the like.

FIG. 2L illustrates a rear view of the wearable therapeutic device 200 in accordance with some embodiments. Wearable therapeutic device 200 may include a top wrap portion of outer shell 222 and a bottom wrap portion of outer shell 222 configured to provide an adjustable fit to a wearer further enhanced by adjustment controllers 204.

Figure 3:
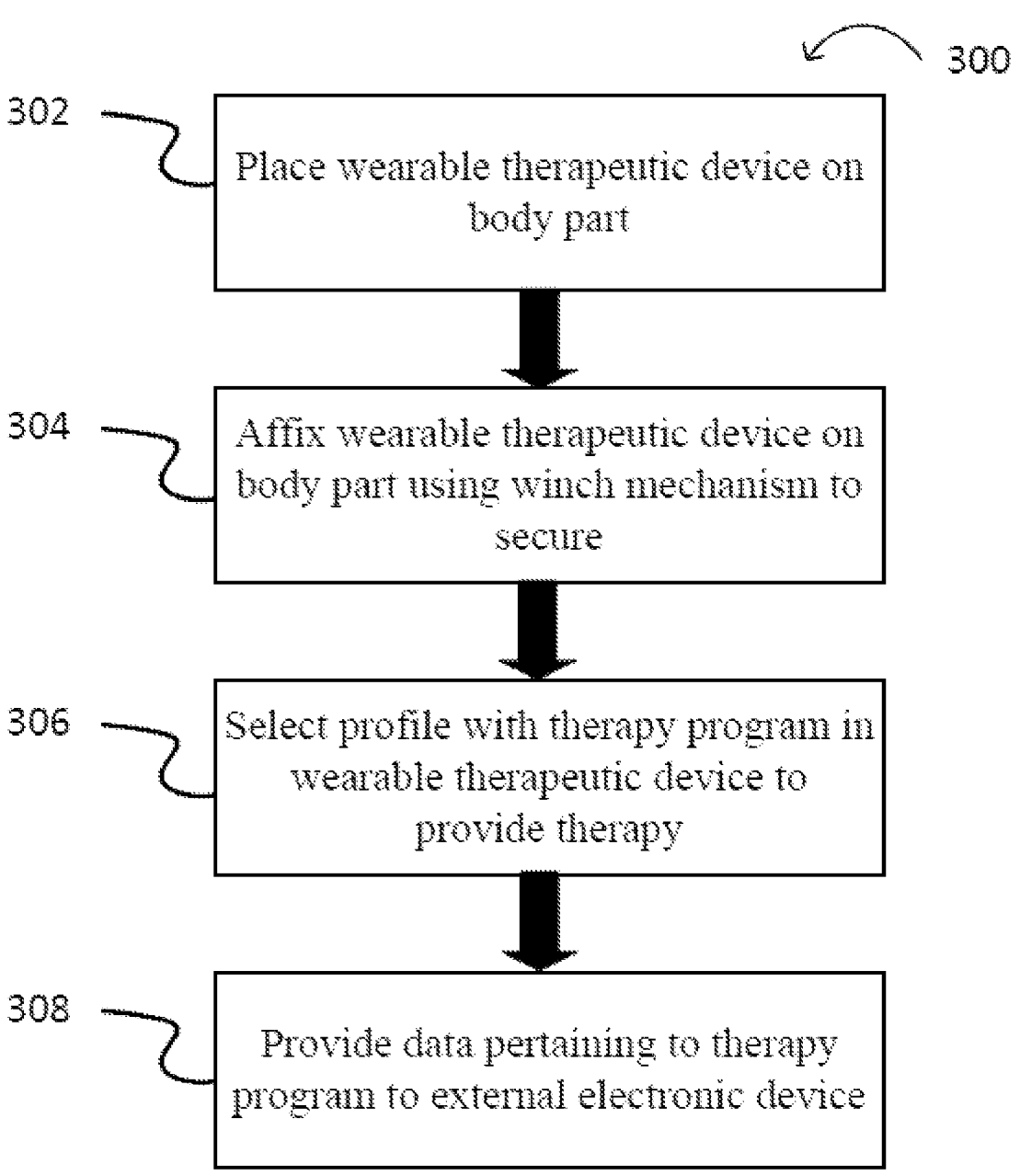
FIG. 3 is a method of providing therapy using a wearable therapeutic device, in accordance with some embodiments.
Figure 4A:
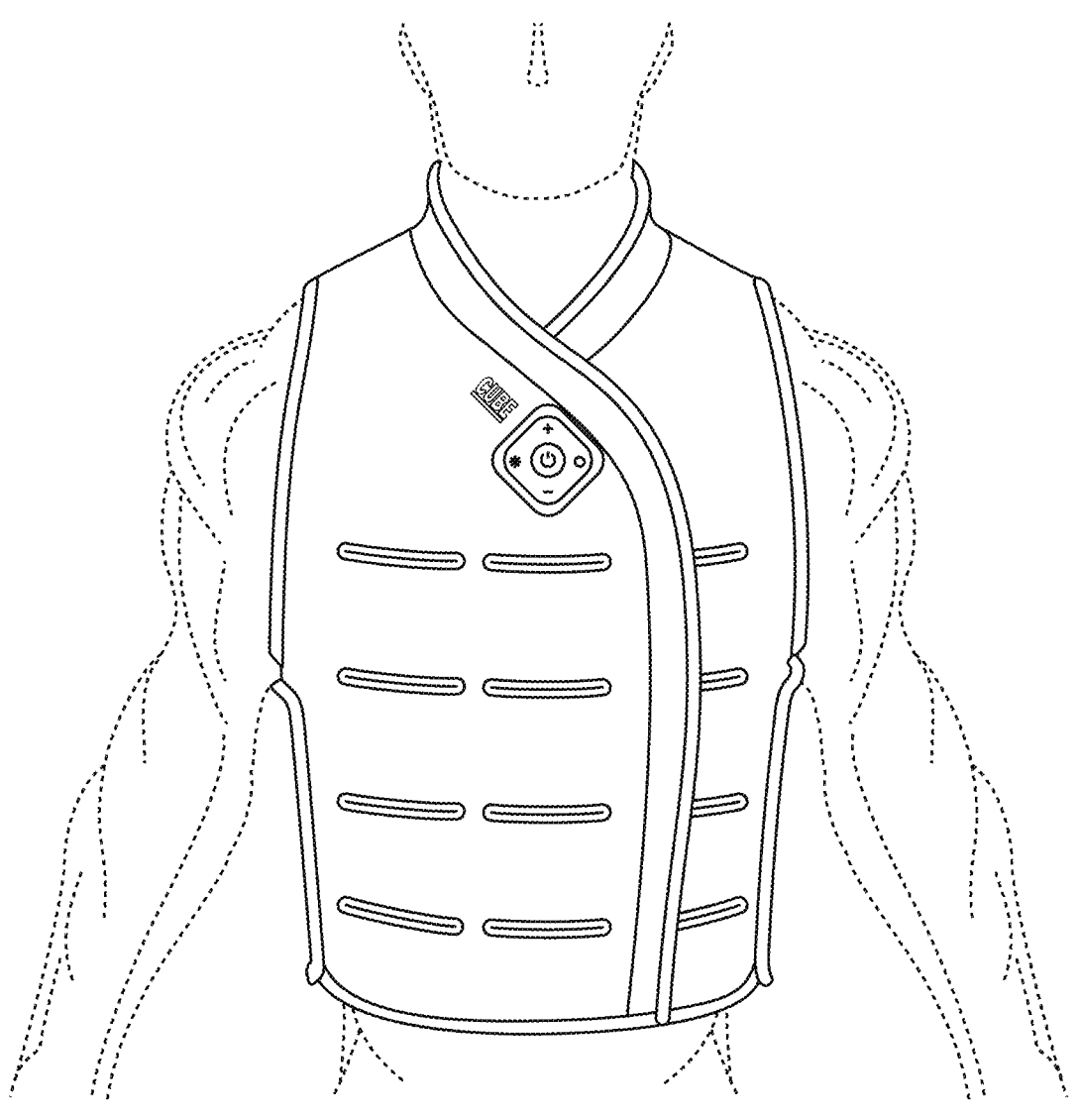
FIGS. 4A-4E depicts embodiments of wearable devices implemented as a vest.
Figure 4B:
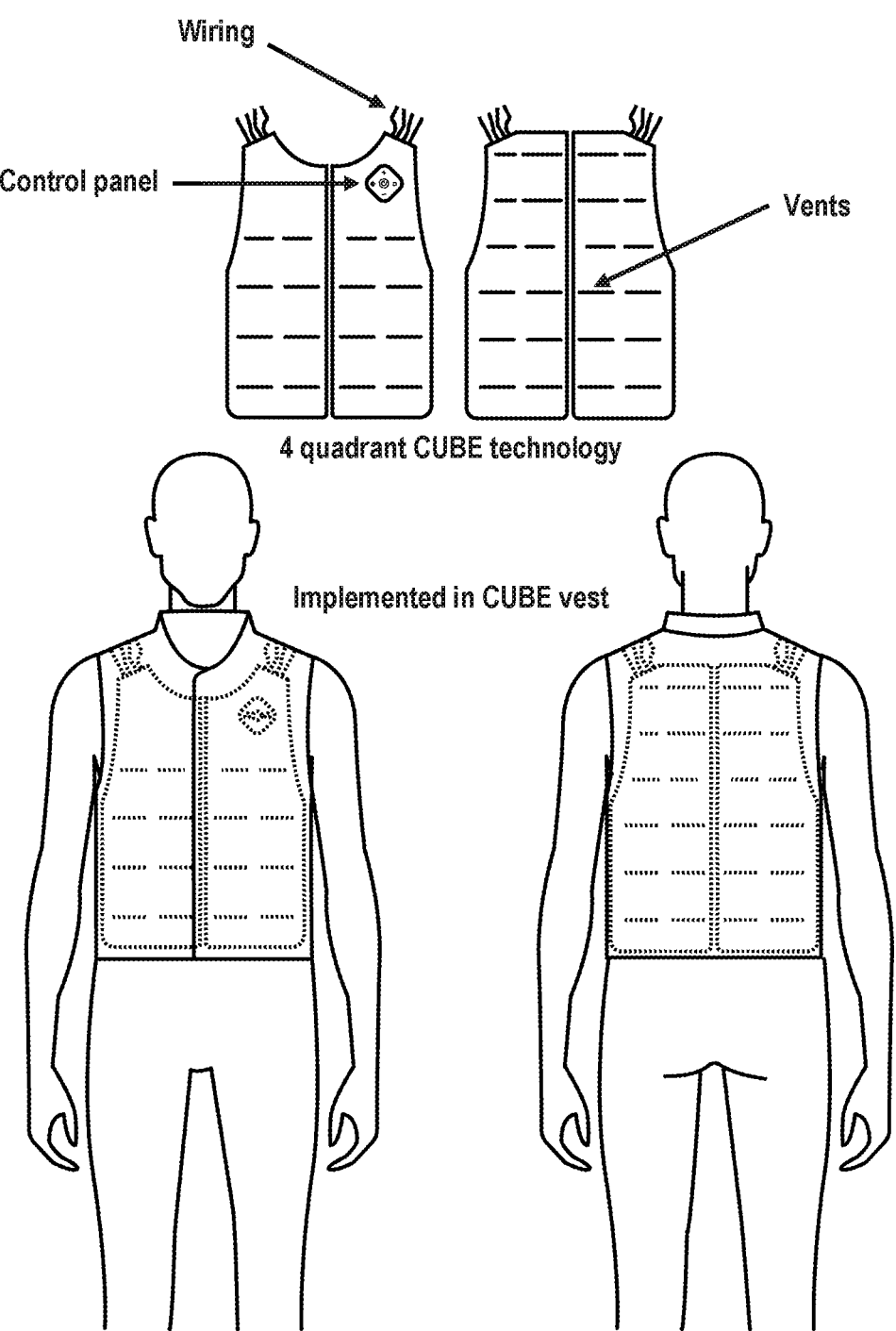
Figure 4C:
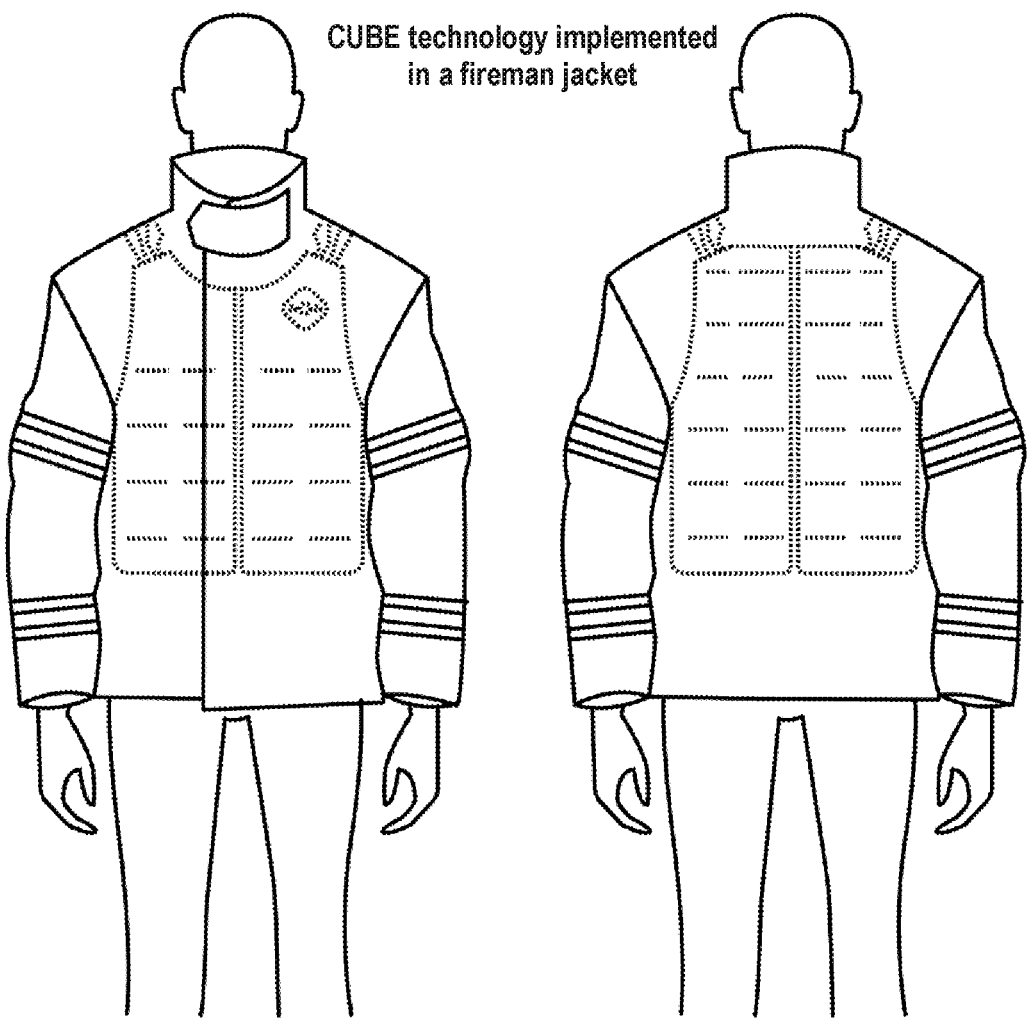
Figure 4D:
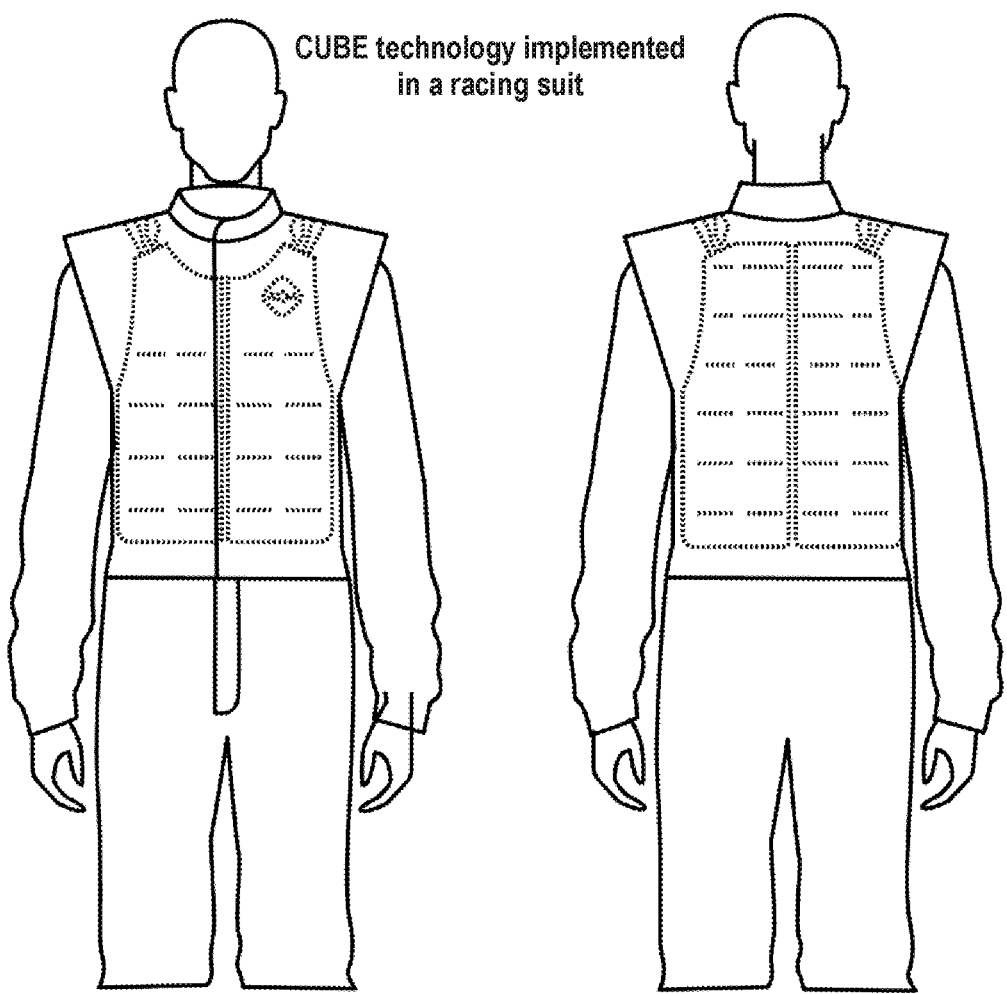
Figure 4E:
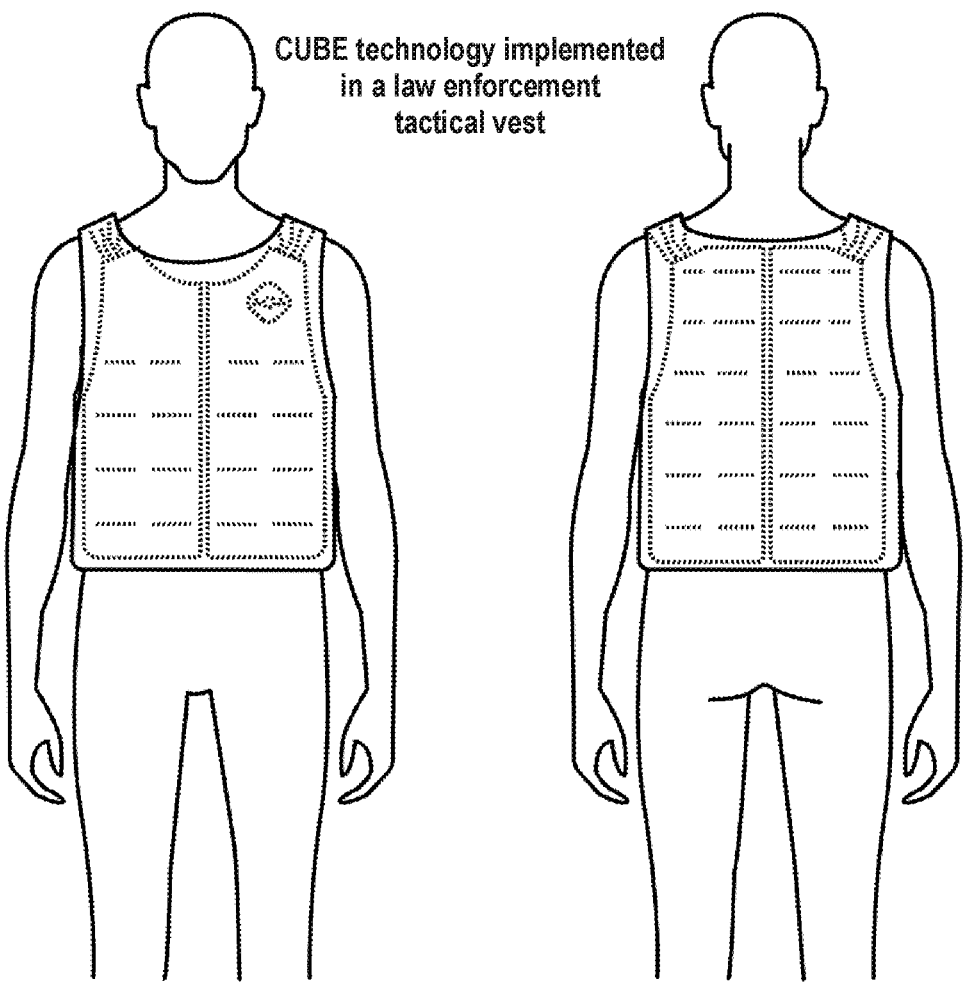

FIG. 3 3 illustrates a method of icing and heating using a wearable device. Method 300 of providing therapeutic recovery may include a first step 302 of placing a wearable therapeutic device on a body part.

The second step 304 of the method may be affixing the wearable therapeutic device on a body part using a winch mechanism to secure the wearable therapeutic device on the body part.

The third step 306 may be selecting a profile with a recovery program in the wearable therapeutic device to cause the wearable device to provide a selectable therapy (e.g., icing and heating) in user-definable time intervals.

The fourth step 308 of the method may be transmitting messages securely to and from the wearable therapeutic device. The messages may be information to or from the user or instructions for operating the wearable therapeutic device.

In some embodiments, the wearable device includes a feedback loop between a controller (like controller 38), the icing elements and heating elements, and various sensors.

In some embodiments, the various sensors may include a heart rate sensor, a pulse oximeter sensor, and various other biometric sensors. The wearable device may further include an epidural layer sensor including a pressure sensor that is configured to function as a predictive tool to estimate a user's expected recovery time. The epidural layer sensor may further be configured to predict a user's susceptibility to re-injury based on various sensors and/or user inputted information including a user diet, amount or quality of sleep, stress, range of motion, height, age, weight, BMI, or the like.

In some embodiments, the wearable device may be configured to prevent or reduce a user from experiencing heat exhaustion.

In some embodiments, the wearable device may be formed in various shapes and sizes, including a rectangular wrap.

In some embodiments, the wearable device transfers heat from its Peltier devices through a liquid bladder like those described above. In some cases, one or more bladders may be utilized to apply therapeutic temperatures to the user's body.

In some embodiments, the wearable device includes a rechargeable power supply to power the electronic components. For example, the wearable device may be a wireless device that allows the wearer flexibility in mobility. The wearable device in some embodiments includes a wirelessly chargeable battery to power the wearable device. In some embodiments, the wearable device includes a removable power bank that can be independently charged.

In some embodiments, the wearable device includes one or more ports supporting connectivity to external devices including external heating or cooling mechanisms.

In some embodiments, the wearable device is capable of rapid cooling by passing gas over heatsinks or other thermal dissipation elements. In some embodiments, the gas passed over the heatsinks or other thermal dissipation elements is carbon dioxide (Co2). In some embodiments, the gas is an inert gas.

In some embodiments, the wearable device is a self-contained unit for ambulatory therapeutic delivery that utilizes gas cartridges and flow metering delivery.

In some embodiments, the wearable device provides non-ambulatory therapy using gas delivered via a port on the wearable device from external tanks or delivery sources.

In some embodiments, the wearable device includes one or more UV light sources for providing antimicrobial/disinfection capabilities. In some embodiments, the UV light sources are used during therapeutic treatment. For example, a wearer of the wearable device is provided with a UV light therapy to site-treat post-surgical wounds. In another example, the UV light source of the wearable device can be used to self-clean the device while not in use or while the device is being charged. In some embodiments, the UV light source of the wearable device can be used to disinfect other devices (e.g., treatment tools).

In some embodiments, the wearable device provides micro-needle delivery of, or sampling of, various substances. In some embodiments, the wearable device provides hydrogel transdermal drug delivery and also passively extract interstitial fluid from the skin of the wearer. In some embodiments, the wearable device provides application of stem cell derivatives such as platelet-rich fibrin (PRF) and platelet-rich plasma (PRP) applications. In some cases, the micro-needles may be in an array on a patch that is applied to an inner surface of the wearable device, such that the wearable device biases the patch against the user's body. A back-side of the patch may have electrical contacts that interface with a controller of the system to control or read data from the patch.

In some embodiments, the wearable device is configured to provide other therapeutic hydrogels and exomes to the wearer. The wearable device may include replaceable or reusable applicators to transport the therapeutic hydrogels and exosomes.

In some embodiments, the wearable device includes a plurality of sensors integrated into the wearable device for collecting data pertaining to usage, activity, therapeutic temperatures, external ambient temperatures, weight/force applied to the limb of the wearable device, and other related data.

FIGS. 4A-4E illustrate various embodiments in which wearable devices like those described above are implemented as a vest. These vests may be used in a variety of professional use cases, like for cooling (or heating) of firefighters, race car drivers, or law-enforcement or military professionals wearing ballistic vests. Or embodiments may be used in non-professional or medical settings.

Some embodiments may include a pressurized container of a flame retardant gas such as haloalkane/Bromochlorodifluoromethane (BCF), Bromotriflouromethane (Halon 1301, Halon 13B1, or BTM), Halon 1211, or other similar gasses, and that gas may be released to the atmosphere through the vest to either cool heat emitting elements or pass through annuluses of a wearable device for such uses but not limited to fire protection wear. Gas can be applied from a source such as a tank or canister and dissipated via mechanical valves or electronically controlled/metered configurations. In some cases, the emitted gas may suppress fire near the user as well.

Some embodiments include the combination of a wearable device utilized for therapeutic delivery to the ankle and foot-wear appendage that attaches to such device. The construction of the foot appendage can vary in size, left or right configurations, and can have characteristics such as arch or other anatomical variances, as well as being constructed of different shapes or materials. In some cases, a first, upper portion may include thermal management hardware (and other sensors and actuators like those described above) and an attachable lower portion may be sized and shaped for the individual user's foot, allowing for a relatively small number of designs of the upper portion to accommodate a wide range of variation in body shape.

Some embodiments include a wearable device containing multiple layers of ballistics protection or fire retardant/protective materials for use in combination with existing protective gear or custom derived wearables that may include cooling or temperature controls.

Figure 5:
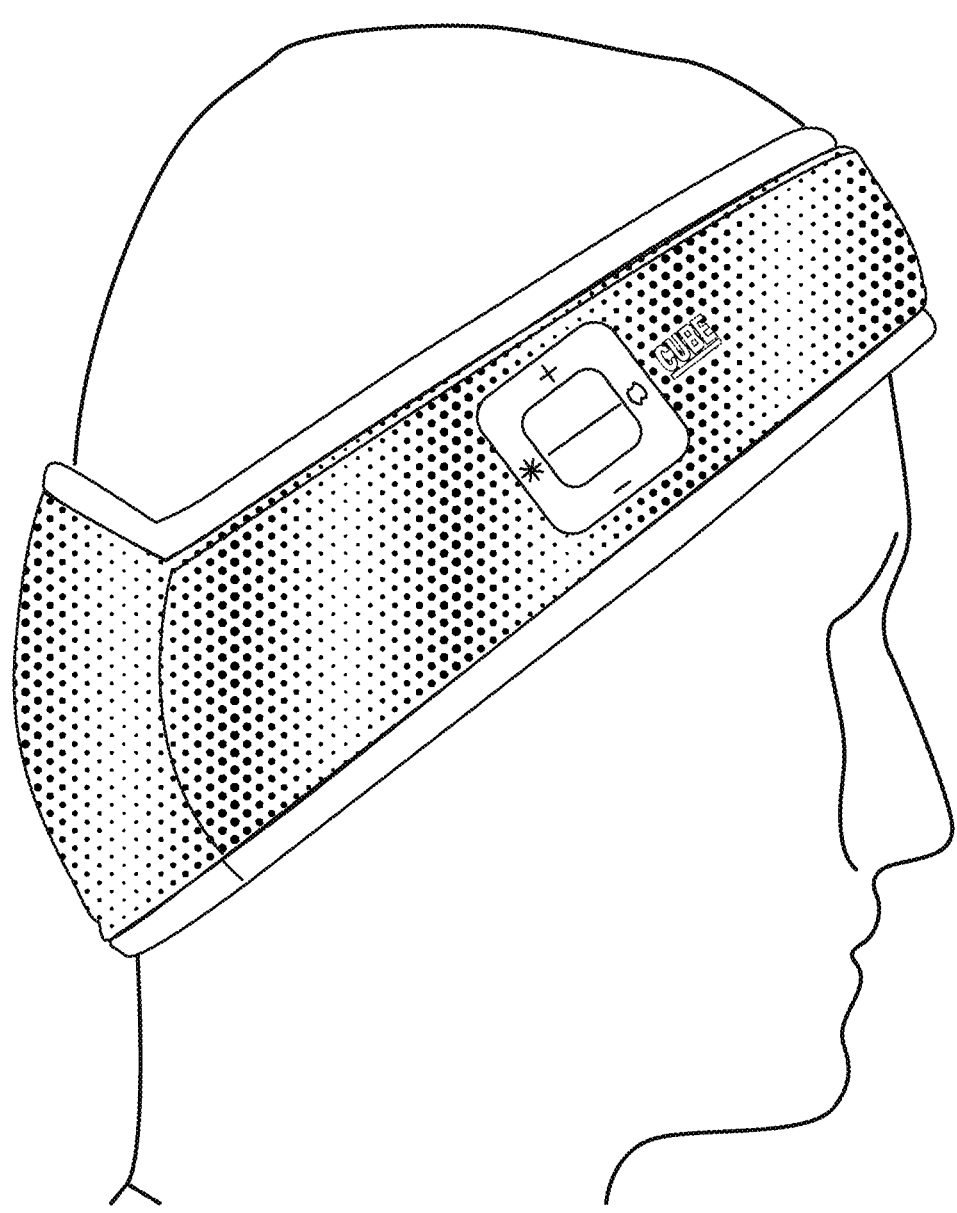
FIG. 5 depicts an embodiment of a wearable device implemented as a headband.

FIG. 5 depicts a head-mounted embodiment that may have the features of the above-described wearable devices. Some embodiments may heat or cool the user's head, or apply various other described stimuli responsive to the various described sensors. Example use cases include potential treatment of head injury, modulating overall body temperature, and managing comfort in hot or cold environments.

Figure 6:
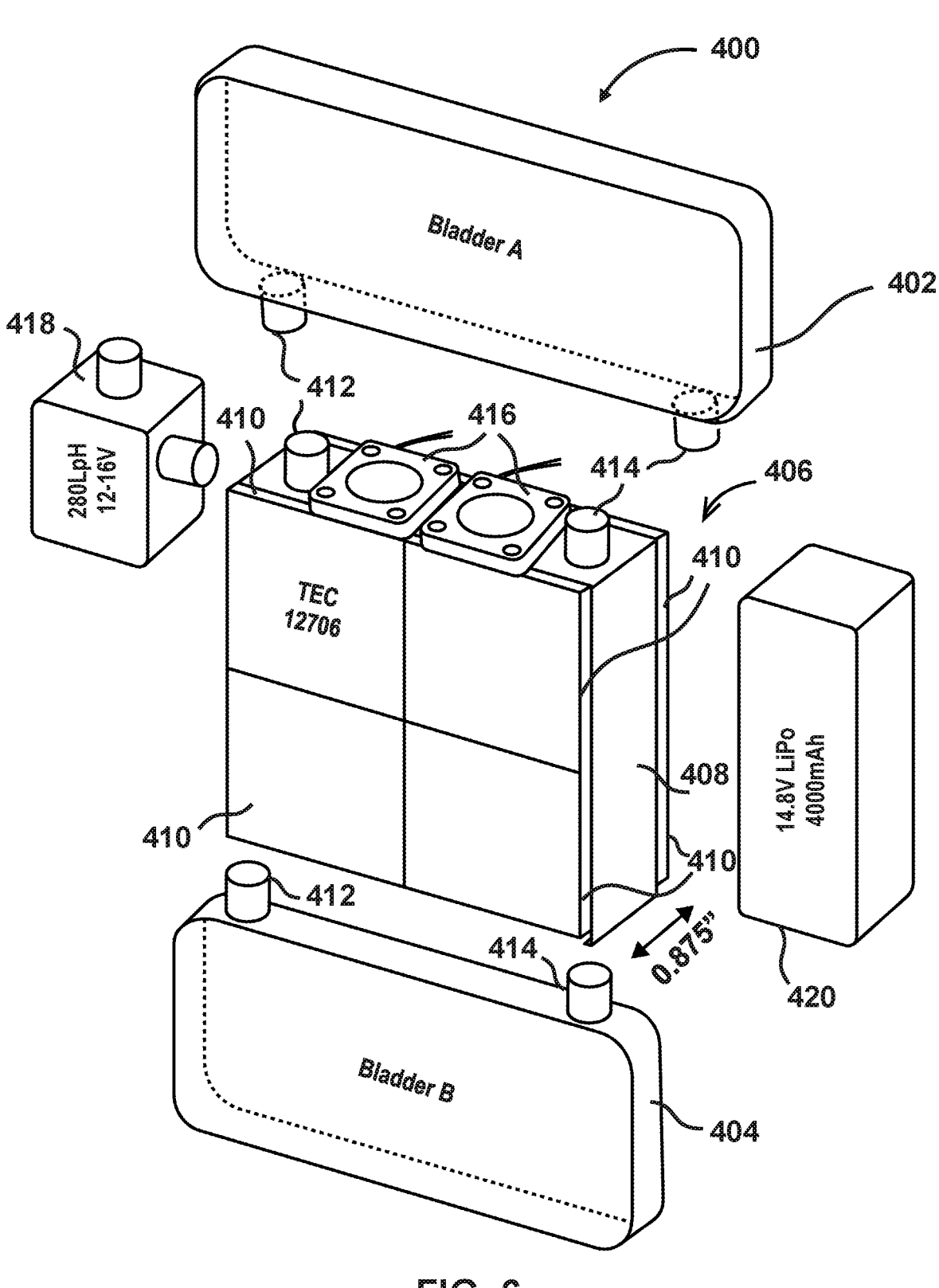
FIG. 6 depicts an example of a dual-bladder module, in accordance with some embodiments.

FIG. 6 is an exploded perspective view of an example of a module for cooling or heating 400 (that may be used with or in place of the above-described module) with dual bladders 402 and 404 and a heat exchanger 406 with a tank 408 flowing a working fluid cooled or heated by 4 or 8 thermoelectric devices 410 arrayed on its outer surface. In some embodiments, a heat sink may be mounted adjacent the thermoelectric devices 410 on one or both faces opposite the tank 408. In some embodiments, the bladders may be connected by tubes and configured to exchange a working fluid with the heat exchanger 406 via inlet and outlet ports 412 and 414 respectively. In some embodiments, the heat exchanger 406 has a pump 418 that drives the flow of the working fluid in a closed loop, or from a hot bladder to a cold bladder or cycles water between the bladders and the heat exchanger 406, either in a single loop or parallel, separate loops. In some embodiments, operation is powered by a battery 420. The thermoelectric devices 410 may be cycled in a manner like that described above, out of phase, with less than a hundred percent duty cycle to operate more efficiently than some other approaches. A pair of fans 416 may circulate air over the thermoelectric devices 410 or a heat sink.

Figure 7:
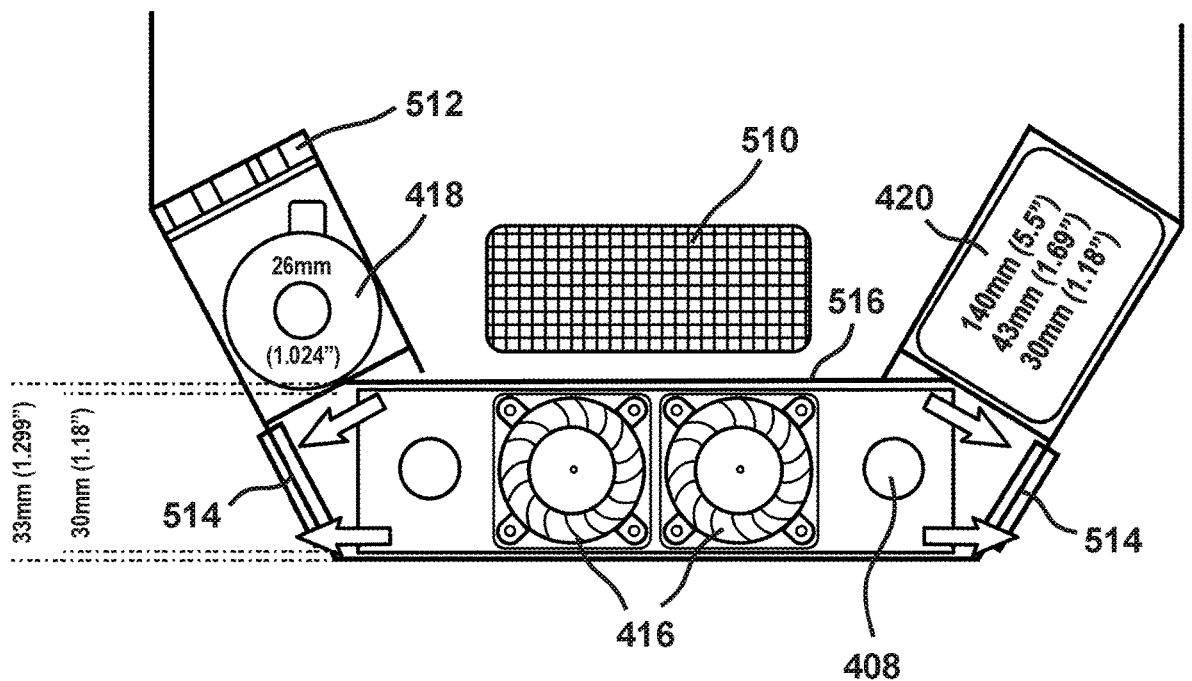
FIG. 7 depicts the module of FIG. 6 installed.

FIG. 7 is a top cross-sectional view of the heat exchanger 406 in a portion of a housing. (The bladders 404 and 402 may be biased against the user's body and connected by tubes via ports 412 and 414.) The heat exchanger may include forced convection fans 416 on top of a heat sink shroud 516 described below with reference to FIG. 8. In some embodiments, cooling ambient air or heating ambient air is drawn in through an air intake 510 and is driven by the fans 416 through the shroud 516 over the thermoelectric devices 410 or a heat sink thereon to be exhausted out the sides through side vents 514. The figure further shows a controller 512 configured to control operation of the pump 418 and other components by drawing power from battery 420.

Figure 8:
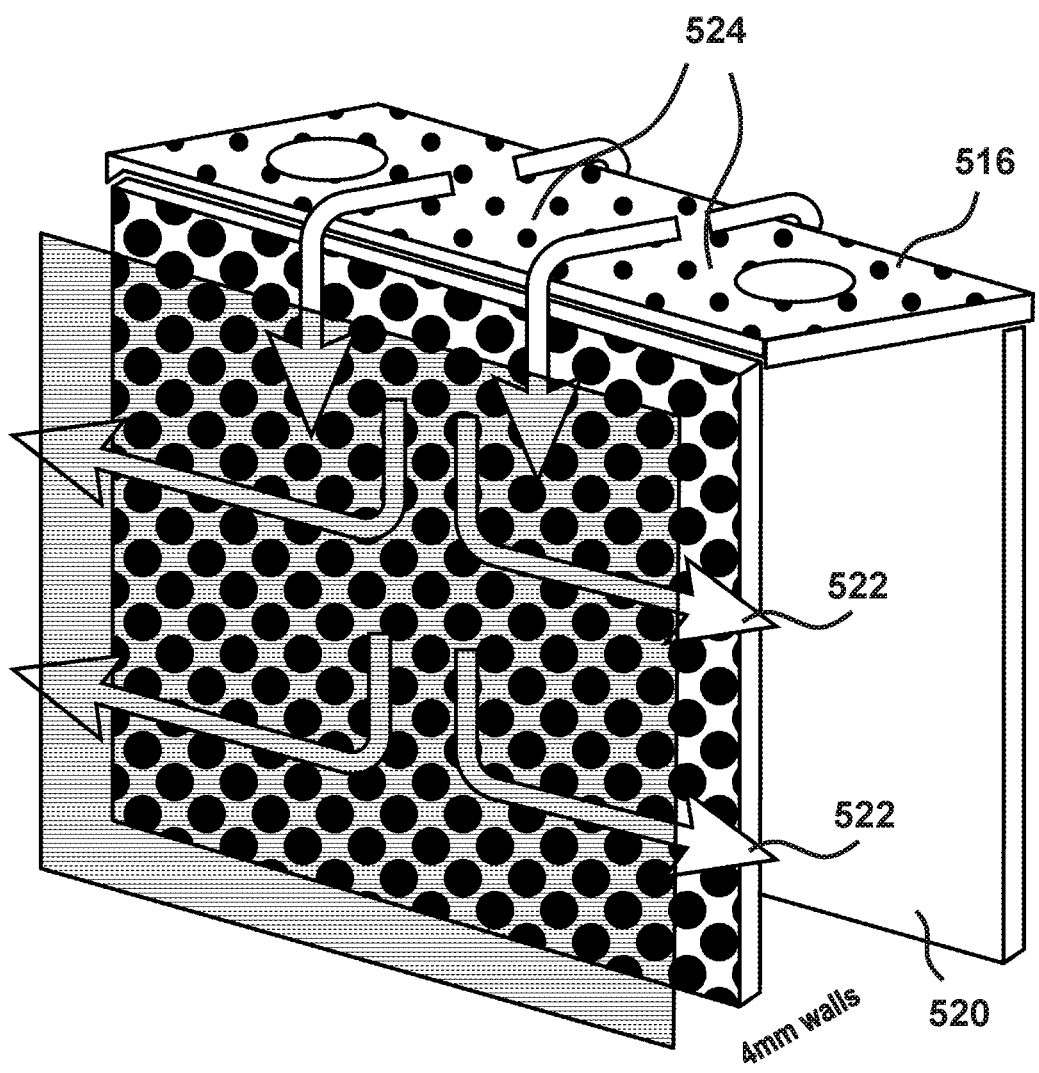
FIG. 8 depicts a shroud in which the module of FIG. 6 may be installed.

FIG. 8 shows an example of shroud 516 in perspective view. In some embodiments, the shroud 516 may include a plurality of apertures, such as two apertures 524 in a top portion, through which air is circulated by the above-described fans 416. In some embodiments, the shroud includes an interior portion 520 into which the heat exchanger 406 is inserted. In some embodiments, air driven by the fans 416 follows the path illustrated by arrows 522, being blown through the interior 520 and along between fins running horizontally of a heat sink on either side of the thermoelectric devices 410 shown above in FIG. 6.

Figure 9:
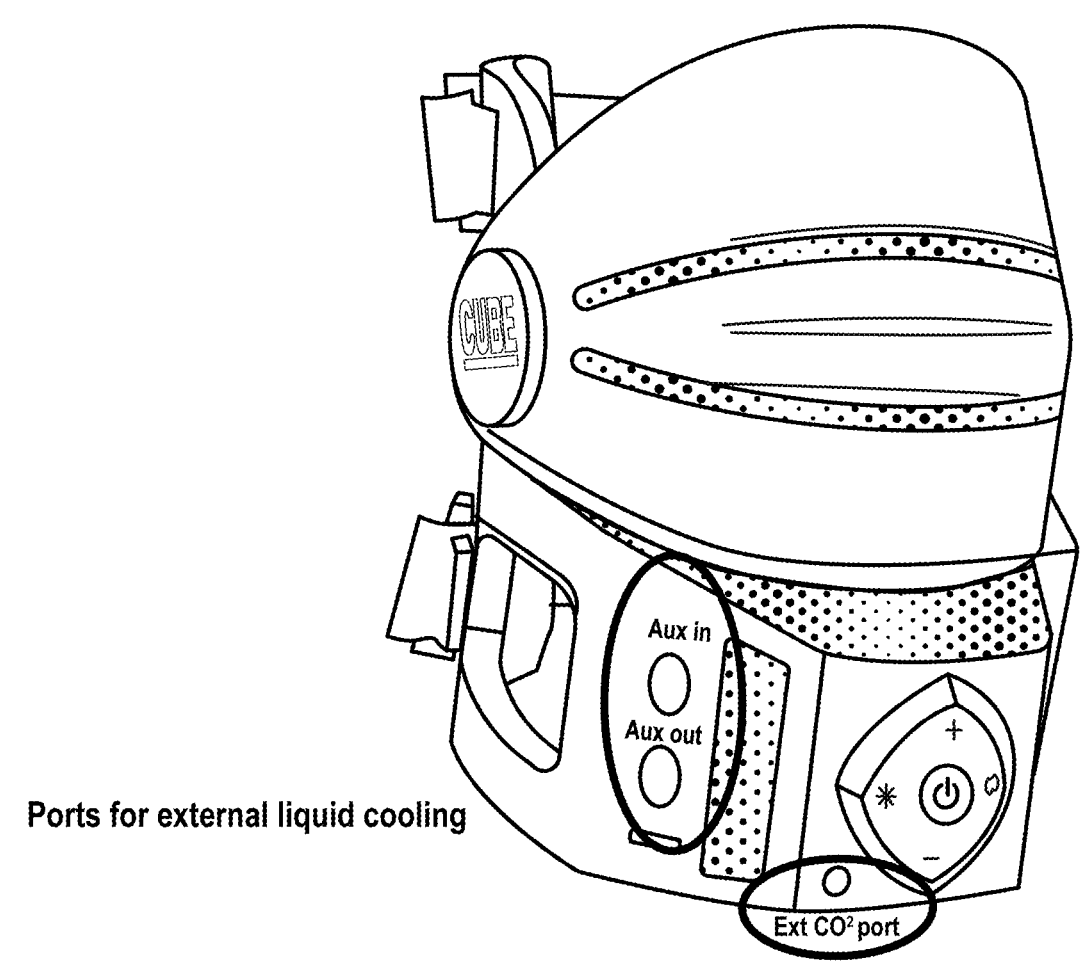
FIG. 9 depicts a knee-brace with ports for external cooling or heating of a working fluid and a port for receiving compressed inert gas.

FIG. 9 is a perspective view of an example of a wearable device with auxiliary input and output ports for external liquid cooling or heating and an external inert gas port by which pressurized inert gases may be released to boost cooling in the manner like that described above.

Figure 10:
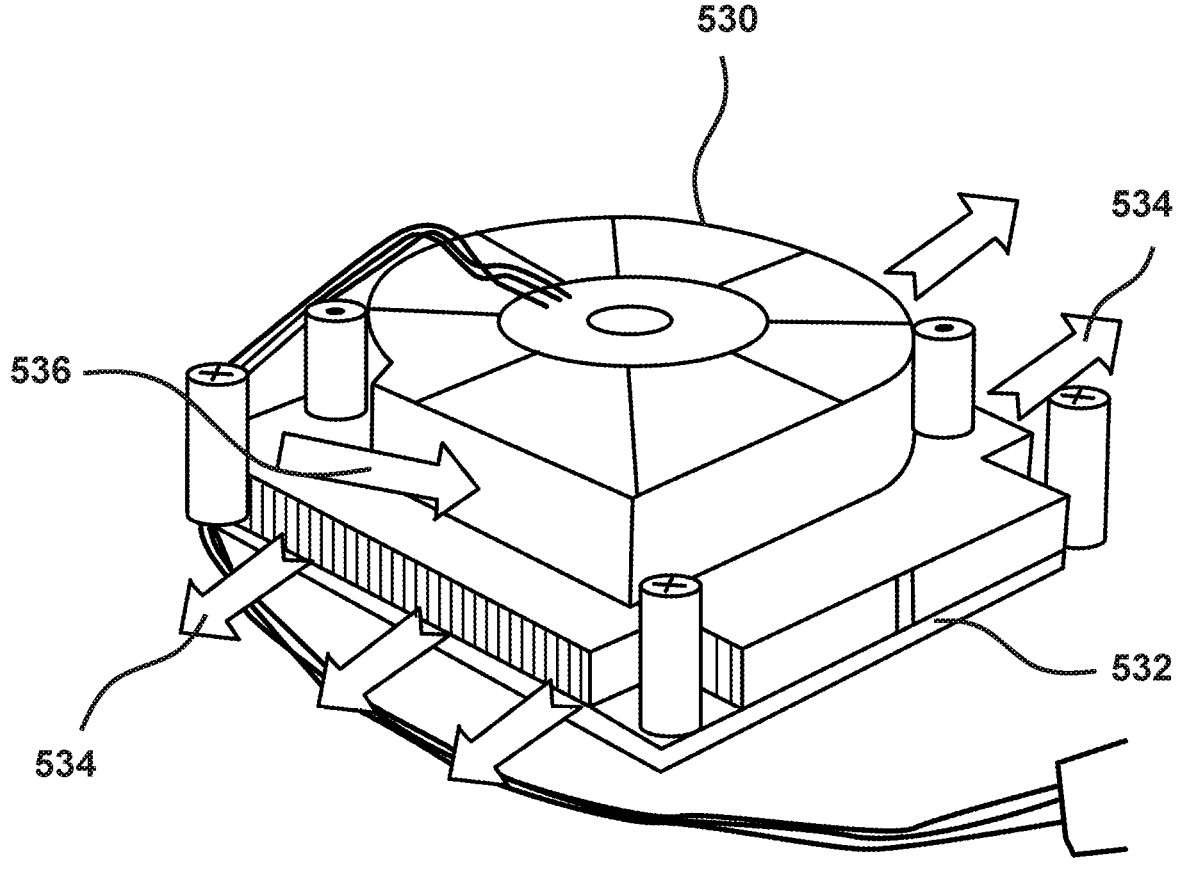
FIG. 10 depicts a heat sink and blower configured to apply compressed inert gas to boost cooling.

FIG. 10 is a perspective view of a heat sink 532 with a blower 530 (or other type of fan) mounted thereon. The heat sink 532 may have its bottom face in the position shown, positioned adjacent the exterior surface of the thermoelectric devices 410 in FIG. 6, in some embodiments. In some embodiments, the blower 530 may drive air flow in the path illustrated by arrows 534 to remove heat or apply heat to the fins of the heat sink 532. In some embodiments, boosts of cooling may be applied by injecting pressurized inert gases through the path illustrated by arrow 536, into the inlet of blower 530.

Figure 11:
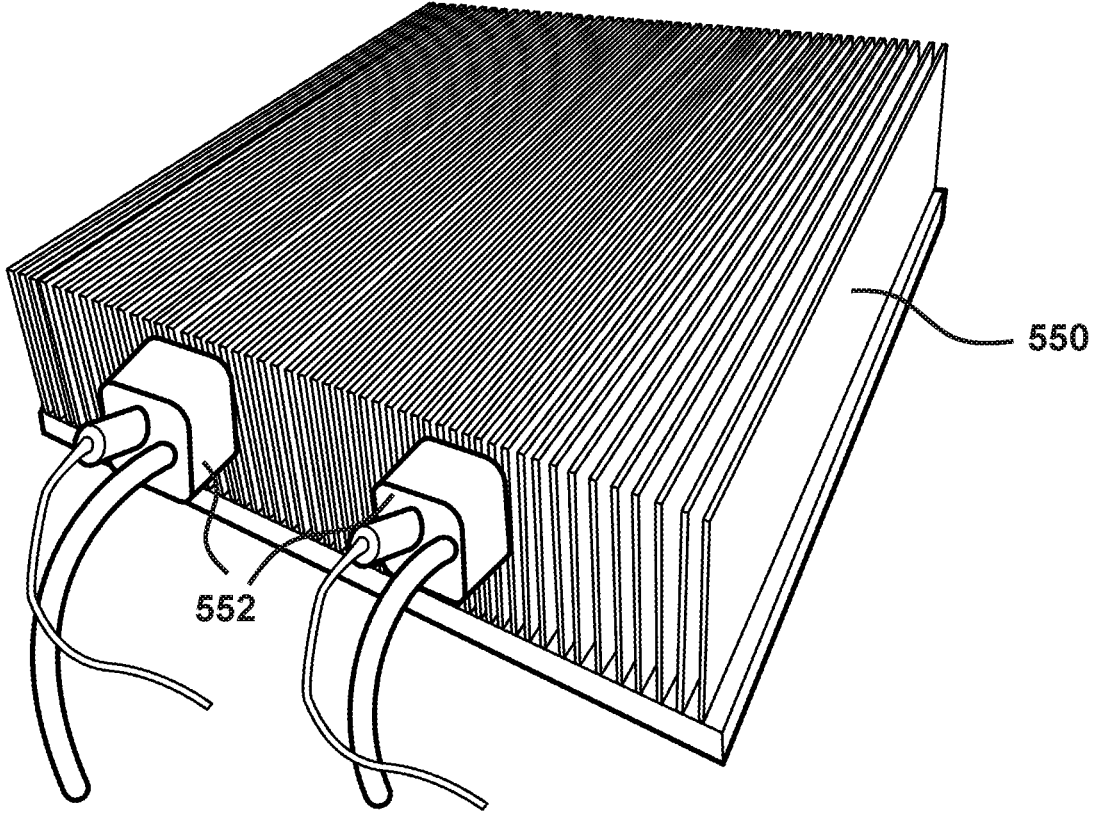
FIG. 11 depicts another heat sink configured to apply compressed inert gas to boost cooling.

FIG. 11 is a perspective view of another example of a heat sink 550 that may be used in a similar manner to that described above. In some embodiments, the heat sink 550 may have positioned thereon electronic valves and nozzles 552 positioned to release pressurized inert gas in between the fins of the heat sink 550. In some embodiments, controlled gas dispensing may occur at one or several places within the fins 550 at the direction of the controller 512 in a manner like that described above.

Figure 12:
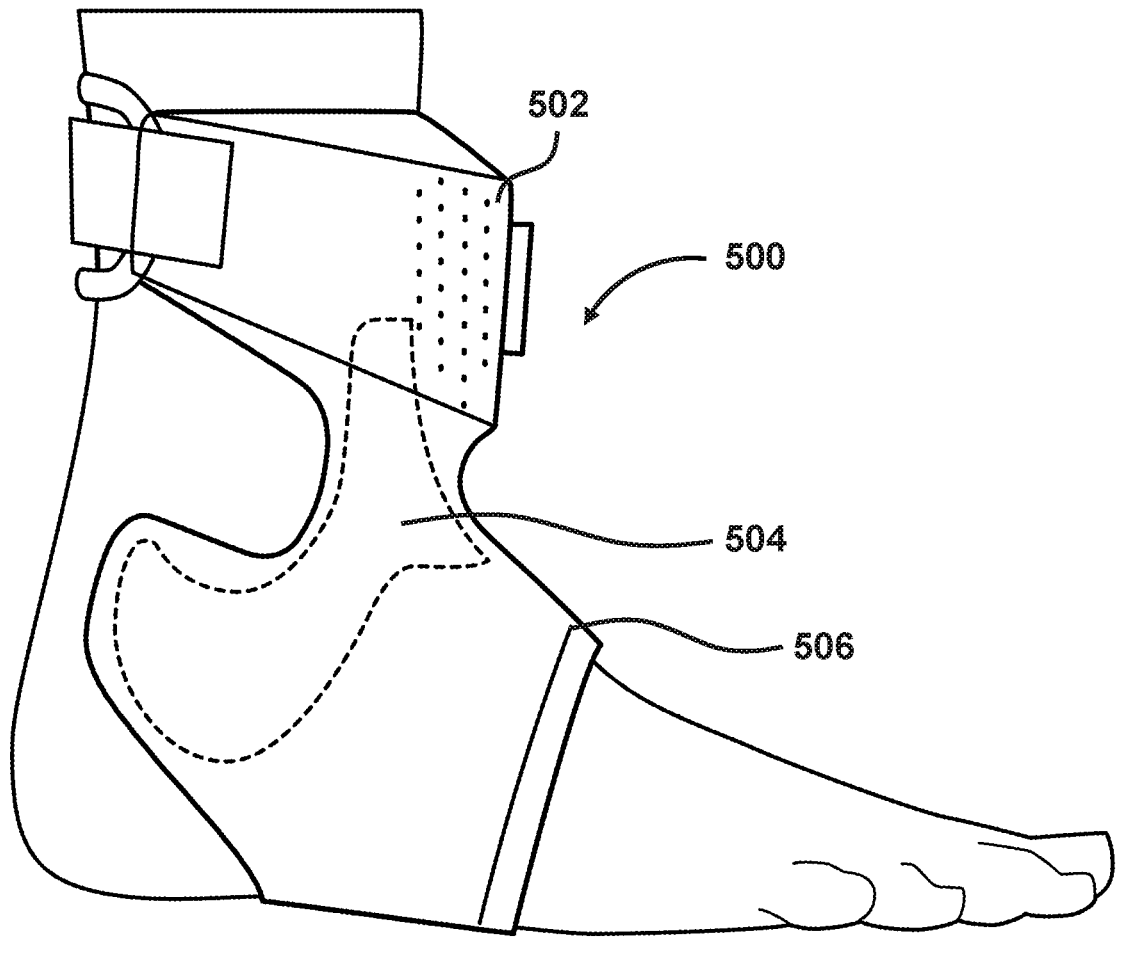
FIGS. 12 and 13 depict left and right side translucent views of an example of an ankle brace with an example of the above-described heating or cooling modules, in accordance with some embodiments.
Figure 13:
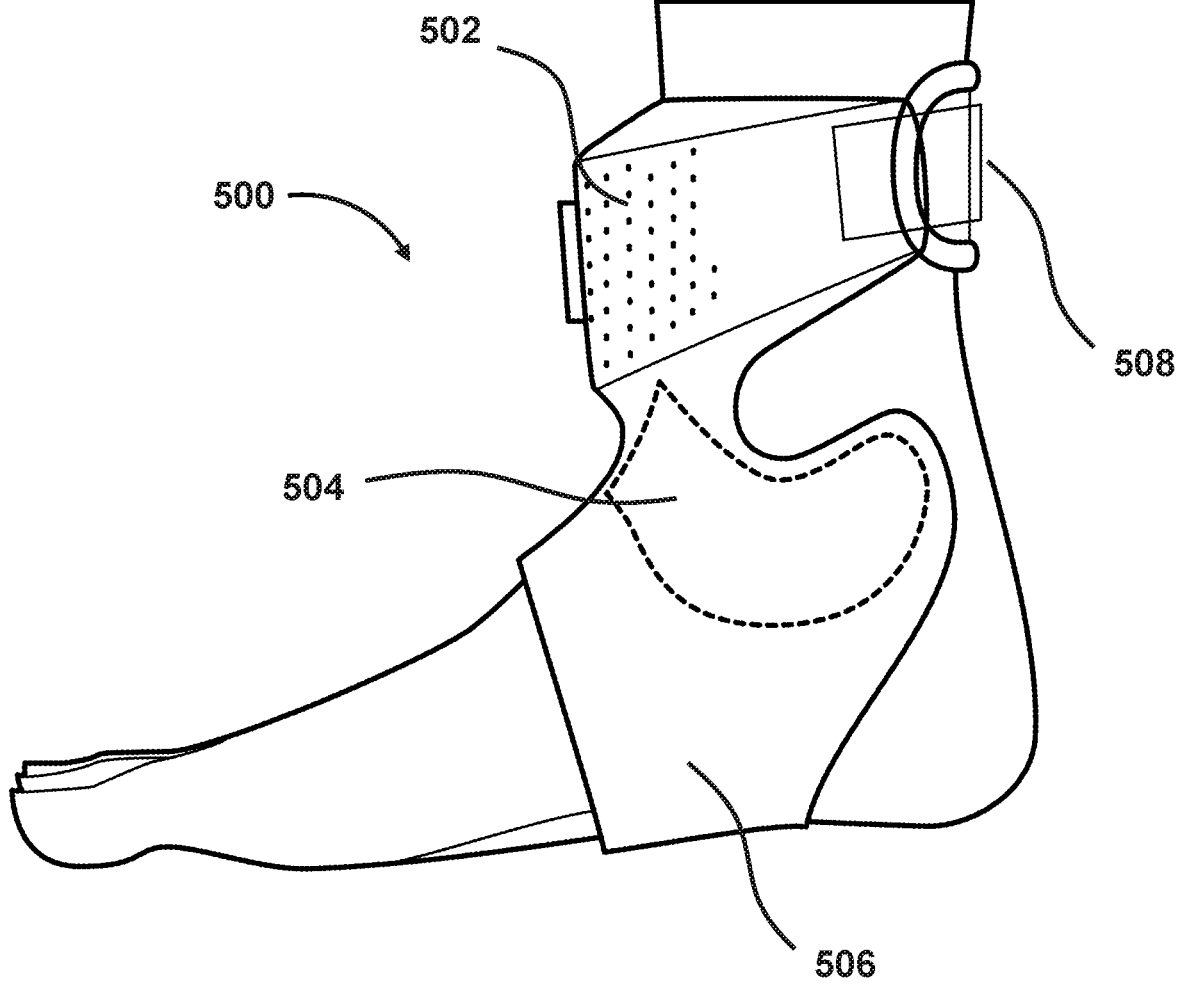

FIGS. 12 and 13 depict left and right side translucent views of an example of an ankle brace with an example of the above-described heating or cooling modules, in accordance with some embodiments. The brace 500, in some embodiments, includes a bladder 504 like that described above, coupled to a heat exchanger in housing 502, which has vents to allow the flow of air. Brace 500 may include a garment 506 to which these components are attached, and the garment may include a clasp 508 configured to attach the brace around the back of the ankle or lower leg. The bladder 504 may extend conformally up the leg to at least in part cover the tendon that is between the tibia and fibula and also may extend lower on the bottom to at least partially cover the area where the top of the foot connects to the calceneus and talus joint. Some embodiments are expected to afford a comformal fit of the bladder to cover the tendon that is in between the tibia and fibula (which are rigid bones) and where the top of the foot connects to the calceneus and talus joint. Rigid heat exchangers are expected to have difficulty targeting this region due to the severe topology (which is not to suggest that rigid heat exchangers or any other material is disclaimed).

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from system 100 may be transmitted to system 100 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g., within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provide by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X' ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A device, comprising: a body-to-liquid heat exchanger, configured to exchange heat between a user's body and a liquid, the body-to-liquid heat exchanger comprising a conformal bladder defining a serpentine portion of a liquid-flow path; a first conduit placing an inlet to the liquid-flow path in fluid communication with an outlet of a liquid-to-ambient-air heat exchanger; a second conduit placing an outlet of the liquid-flow path in fluid communication with an inlet of the liquid-to-ambient-air heat exchanger; and the liquid-to-ambient-air heat exchanger coupled to the first conduit and the second conduit, the liquid-to-ambient-air heat exchanger comprising: a pump in fluid communication with the liquid-flow path; a tank comprising another serpentine portion of the liquid-flow path; a first and a second Peltier thermoelectric cooler adjacent the tank and in thermal communication with the liquid-flow path; a heat sink adjacent the first and second Peltier thermoelectric coolers, with the first and second Peltier thermoelectric coolers being disposed between the tank and the heat sink; a fan configured to blow air onto fins of the heat sink; and a battery configured to provide electrical power to the first and second Peltier thermoelectric coolers, the pump, and the fan.

2. The device of embodiment 1, comprising: a compressed-gas container; a valve positioned to release gas from the compressed-gas container responsive to a signal from a controller; a channel into which the valve is positioned to direct the gas, the channel being configured to cause the gas to flow adjacent the heat sink to remove heat from the heat sink when the gas is released by the valve.

3. The device of embodiment 2, wherein the channel is configured to recirculate the gas through multiple cooling cycles against the heat sink.

4. The device of embodiment 2, wherein the channel comprises a baffle and an actuator configured to cause the gas to stop being recirculated and ambient air to instead be circulated responsive to the gas exceeding a threshold temperature.

5. The device of embodiment 1, comprising four or more Peltier thermoelectric coolers adjacent the tank and in thermal communication with the liquid-flow path, wherein the Peltier thermoelectric coolers are also configured to apply heat to the user's body at different times from when the Peltier thermoelectric coolers are cooling the user's body.

6. The device of embodiment 1, comprising: a garment attached to the body-to-liquid heat exchanger and configured to position the body-to-liquid heat exchanger adjacent the user's body.

7. The device of embodiment 6, wherein the garment comprises a plurality of body-to-liquid heat exchangers.

8. The device of embodiment 6, wherein the garment comprises a winch configured to bias the garment against the user's body.

9. The device of embodiment 6, wherein the garment is a vest.

10. The device of embodiment 6, wherein the garment is a knee brace.

11. The device of embodiment 6, wherein the garment is an ankle brace.

12. The device of embodiment 6, wherein the garment is a head band or hat.

13. The device of embodiment 1, comprising a controller configured to drive the first and second Peltier thermoelectric coolers on a periodic cycle with less than 100% duty cycle and out of phase with respect to one another.

14. The device of embodiment 1, comprising: an array of needles configured to be selectively actuated by a controller to penetrate skin of the user's body.

15. The device of embodiment 14, wherein: the array of needles is configured to effectual transdermal delivery of an injected material.

16. The device of embodiment 15, wherein: the material comprises a stem cell derivative.

17. The device of embodiment 15, wherein: the material is blood plasma.

18. The device of embodiment 15, wherein: the material is fibrin.

19. The device of embodiment 14, wherein: the array of needles is configured to sample a fluid from the person wearing the garment, the array of needles having or being coupled to a biometric sensor configured to assay the fluid.

20. The device of embodiment 14, comprising: a hydrogel adjacent at least some needles in the array of needles.

We claim:

1. A device, comprising:
a body-to-liquid heat exchanger, configured to exchange heat between a user's body and a liquid, the body-to-liquid heat exchanger comprising a conformal bladder defining a serpentine portion of a liquid-flow path, the bladder having a stress-relief aperture on an edge of the bladder and another aperture surrounded on all sides by the bladder and configured to receive a joint of the user;
a first conduit placing an inlet to the liquid-flow path in fluid communication with an outlet of a liquid-to-ambient-air heat exchanger;
a second conduit placing an outlet of the liquid-flow path in fluid communication with an inlet of the liquid-to-ambient-air heat exchanger;
the liquid-to-ambient-air heat exchanger coupled to the first conduit and the second conduit, the liquid-to-ambient-air heat exchanger comprising:
a pump in fluid communication with the liquid-flow path;
a tank comprising another serpentine portion of the liquid-flow path;
a Peltier thermoelectric cooler adjacent the tank and in thermal communication with the liquid-flow path;
a heat sink adjacent the Peltier thermoelectric cooler, with the Peltier thermoelectric cooler being disposed between the tank and the heat sink;
a fan configured to blow air onto fins of the heat sink; and
a battery configured to provide electrical power to the Peltier thermoelectric cooler, the pump, and the fan;
a valve positioned to release gas from a compressed-gas container responsive to a signal from a controller; and
a channel into which the valve is positioned to direct the gas, the channel being configured to cause the gas to flow adjacent the heat sink to remove heat from the heat sink when the gas is released by the valve.

2. The device of claim 1, wherein the channel is configured to recirculate the gas through multiple cooling cycles against the heat sink.

3. The device of claim 1, wherein the channel comprises a baffle and an actuator configured to cause the gas to stop being recirculated and ambient air to instead be circulated responsive to the gas exceeding a threshold temperature.

4. The device of claim 1, comprising four or more Peltier thermoelectric coolers adjacent the tank and in thermal communication with the liquid-flow path, wherein the Peltier thermoelectric coolers are also configured to apply heat to the user's body at different times from when the Peltier thermoelectric coolers are cooling the user's body.

5. The device of claim 1, comprising:
a garment attached to the body-to-liquid heat exchanger and configured to position the body-to-liquid heat exchanger adjacent the user's body.

6. The device of claim 5, wherein the garment comprises a plurality of body-to-liquid heat exchangers.

7. The device of claim 5, wherein the garment comprises a winch configured to bias the garment against the user's body.

8. The device of claim 5, wherein the garment is a vest.

9. The device of claim 5, wherein the garment is a knee brace.

10. The device of claim 5, wherein the garment is an ankle brace.

11. The device of claim 5, wherein the garment is a head band or hat.

12. The device of claim 1, comprising a controller configured to drive the Peltier thermoelectric cooler and another Peltier thermoelectric cooler on a periodic cycle with less than 100% duty cycle and out of phase with respect to one another.

13. The device of claim 1, comprising:

an array of needles disposed on a patch applied to an inner surface of the device, the array of needles configured to be selectively actuated by a controller to penetrate skin of the user's body.

14. The device of claim 13, wherein:

the array of needles is configured to effectuate transdermal delivery of an injected material.

15. The device of claim 14, wherein:

the material comprises a stem cell derivative.

16. The device of claim 14, wherein:

the material is blood plasma.

17. The device of claim 14, wherein:

the material is fibrin.

18. The device of claim 13, wherein:

the array of needles is configured to sample a fluid from a person wearing the device, the array of needles having or being coupled to a biometric sensor configured to assay the fluid.

19. The device of claim 13, comprising:

a hydrogel adjacent at least some needles in the array of needles.

20. A device, comprising:

a body-contacting heat exchanger configured to provide heat to a user's body, the body-contacting heat exchanger comprising a flexible panel;

an actuator disposed on a side of the body-contacting heat exchanger away from the user's body, the actuator comprising at least one air bladder;

a conduit placing the actuator in fluid communication with a compressor;

the compressor configured to pressurize the actuator;

a heater associated with the body-contacting heat exchanger;

a controller operatively coupled to the heater and the compressor;

a valve positioned to release gas from a compressed-gas container responsive to a signal from the controller;

a channel into which the valve is positioned to direct the gas, the channel being configured to cause the gas to flow adjacent to a heat sink to remove heat from the heat sink when the gas is released by the valve; and a battery configured to provide electrical power to the heater, the compressor, and the controller, wherein, when the actuator is pressurized, the actuator presses the body-contacting heat exchanger against the user's body while the controller operates the heater to maintain a target temperature at the body-contacting heat exchanger.

21. The device of claim 20, further comprising:

a thermally reflective layer on a side of the body-contacting heat exchanger away from the user's body; and a layer adjacent the user's skin.

22. The device of claim 20, wherein the heater is a body-to-liquid heat exchanger configured to receive heated liquid from an ambient-to-liquid heat exchanger and transfer heat from the liquid to the user's body.

23. The device of claim 22, wherein the body-to-liquid heat exchanger comprises thermoelectric devices, a heat sink, and a fan, and the controller drives the thermoelectric devices with less than 100% duty cycle and out of phase.

24. The device of claim 20, wherein:

the device is configured to be worn across a joint region, the body-contacting heat exchanger being positionable adjacent the joint and the actuator being disposed on a side of the body-contacting heat exchanger opposite a skin-contacting surface and arranged about an axis of rotation of the joint; and when pressurized, the actuator presses the body-contacting heat exchanger against the user's body while permitting relative rotation about the axis of rotation.

25. The device of claim 24, wherein the joint region comprises an ankle.

26. The device of claim 20, wherein the device is wearable as a brace and further comprises straps or a winch configured to bias the brace against the user's body.

27. The device of claim 20, further comprising a temperature sensor on the body-contacting heat exchanger.

* * * * *